(12) United States Patent
Ewald et al.

(10) Patent No.: US 10,545,133 B2
(45) Date of Patent: Jan. 28, 2020

(54) MOLECULAR SIGNATURES OF INVASIVE CANCER SUBPOPULATIONS

(71) Applicant: The Johns Hopkins University, Baltimore, MD (US)

(72) Inventors: Andrew Josef Ewald, Catonsville, MD (US); Kevin Cheung, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 602 days.

(21) Appl. No.: 14/276,099

(22) Filed: May 13, 2014

(65) Prior Publication Data

US 2014/0336282 A1 Nov. 13, 2014

Related U.S. Application Data

(60) Provisional application No. 61/915,050, filed on Dec. 12, 2013, provisional application No. 61/822,713, filed on May 13, 2013.

(51) Int. Cl.
*G01N 33/50* (2006.01)

(52) U.S. Cl.
CPC ............... *G01N 33/5011* (2013.01)

(58) Field of Classification Search
CPC ............... G01N 33/574; G01N 33/5005
See application file for complete search history.

(56) References Cited

U.S. PATENT DOCUMENTS

| | | | |
|---|---|---|---|
| 5,846,536 A | 12/1998 | Bissell et al. | |
| 6,123,941 A | 9/2000 | Bissell et al. | |
| 6,828,111 B2 | 12/2004 | Shekhar et al. | |
| 2008/0070270 A1* | 3/2008 | Costello ............. | G01N 33/5011 435/29 |
| 2010/0255528 A1 | 10/2010 | Zudaire et al. | |
| 2011/0053185 A1 | 3/2011 | Rustgi et al. | |
| 2011/0085982 A1 | 4/2011 | Seewaldt et al. | |
| 2011/0201669 A1 | 8/2011 | Cao | |

OTHER PUBLICATIONS

Rakha et al (Journal of Pathology, 2006, vol. 208, pp. 495-506).*
Robinson, PLoS Biology, 2004, vol. 1, pp. 0018-0020.*
The abstract of Costello et al (Journal of Clinical Oncology, 2006, vol. 24, No. 18S (Jun. 20 Supplement), abstract No. 11509).*
Hoelzinger et al (Neoplasia, 2005, vol. 7, pp. 7-16).*
The abstract of Warren et al (Journal of Urology, 2009, vol. 181, No. 4, Supplement, p. 217, abstract No. 608).*
Westphal et al (Methods in Molecular Biology, 1990, vol. 5, pp. 113-131) (Year: 1990).*
Bulbul et al (Journal of Urology, 1986, vol. 136, pp. 512-516) (Year: 1986).*
Buccione et al (Cancer Metastasis Review, 2009, vol. 28, pp. 137-149) (Year: 2009).*
Tseng et al (Journal of Biological Chemistry, 1981, vol. 256, pp. 3361-3365) (Year: 1981).*
Schor et al (International Journal of Cancer, 1982, vol. 29, pp. 57-62) (Year: 1982).*
Abstract of Nguyen-Ngoc et al (ASCB, Dec. 2010, Abstract No. 2351/B868) (Year: 2010).*
Gomm et al (Analytical Biochemistry, 1995, vol. 226, pp. 91-99) (Year: 1995).*
Almendro, A., et al., "Cellular heterogeneity and molecular evolution in cancer" Annu. Rev. Pathol., 8 (2013), pp. 277-302.
Condeelis, J., et al., "Macrophages: obligate partners for tumor cell migration, invasion, and metastasis" Cell, 124 (2006), pp. 263-266.
Conklin, M., et al., "Aligned collagen is a prognostic signature for survival in human breast carcinoma" Am. J. Pathol., 178 (2011), pp. 1221-1232.
Conklin, M., et al., "Why the stroma matters in breast cancer: Insights into breast cancer patient outcomes through the examination of stromal biomarkers" Cell Adh Migr., 6 (2012), 249-260.
De Silva Rudland, S., et al., "Statistical association of basal cell keratins with metastasis-inducing proteins in a prognostically unfavorable group of sporadic breast cancers" Am. J. Pathol., 179 (2011), pp. 1061-1072.
Denardo, D., et al., "CD4(+) T cells regulate pulmonary metastasis of mammary carcinomas by enhancing protumor properties of macrophages" Cancer Cell, 16 (2009), pp. 91-102.
Diaz, L., et al., "Triple negative breast carcinoma and the basal phenotype: from expression profiling to clinical practice", Adv Anat Pathol (2007) 14:419-430.
Egeblad, M., et al., "Tumors as organs: complex tissues that interface with the entire organism" Dev. Cell. 18 (2010), pp. 884-901.
Egeblad, M., et al., "Dynamic interplay between the collagen scaffold and tumor evolution" Curr. Opin. Cell Biol., 22 (2010), pp. 697-706.
Ewald, A., et al., "Collective epithelial migration and cell rearrangements drive mammary branching morphogenesis" Dev. Cell, 14 (2008), pp. 570-581.

(Continued)

*Primary Examiner* — Karen A. Canella
(74) *Attorney, Agent, or Firm* — Johns Hopkins Technology Ventures

(57) ABSTRACT

Carcinomas typically invade as a cohesive multicellular unit, a process termed collective invasion. It remains unclear how different subpopulations of cancer cells contribute to this process. We developed three-dimensional (3D) organoid assays to identify the most invasive cancer cells in primary breast tumors. Collective invasion was led by specialized cancer cells that were defined by their expression of basal epithelial genes, such as cytokeratin-14 (K14) and p63. Furthermore, K14+ cells led collective invasion in the major human breast cancer subtypes. Importantly, lumenal cancer cells were observed to convert phenotypically to invasive leaders following induction of basal epithelial genes. Although only a minority of cells within lumenal tumors expressed basal epithelial genes, knockdown of either K14 or p63 was sufficient to block collective invasion. Our data reveal that heterotypic interactions between epithelial subpopulations are critical to collective invasion. We suggest that targeting the basal invasive program could limit metastatic progression.

7 Claims, 20 Drawing Sheets

(56) References Cited

OTHER PUBLICATIONS

Ewald, A., et al., "Dynamic, long-term in vivo imaging of tumor-stroma interactions in mouse models of breast cancer using spinning-disk confocal microscopy" Cold Spring Harb Protoc. (2011): pdb.top97.

Ewald, A., "Practical considerations for long-term time-lapse imaging of epithelial morphogenesis in three-dimensional organotypic cultures" Cold Spring Harb. Protoc., 2013 (2013), pp. 100-117.

Fidler, P., "The pathogenesis of cancer metastasis: the 'seed and soil' hypothesis revisited" Nat. Rev. Cancer, 3 (2003), pp. 453-458.

Friedl, P., et al., "Collective cell migration in morphogenesis, regeneration and cancer" Nat. Rev. Mol. Cell Biol., 10 (2009), pp. 445-457.

Friedl, P., et al., "Classifying collective cancer cell invasion" Nat. Cell Biol., 14 (2012), pp. 777-783.

Gaggioli, C., et al., "Fibroblast-led collective invasion of carcinoma cells with differing roles for RhoGTPases in leading and following cells" Nat. Cell Biol., 9 (2007), pp. 1392-1400.

Gordon, L., et al., "Breast cell invasive potential relates to the myoepithelial phenotype" Int. J. Cancer, 106 (2003), pp. 8-16.

Gray, et al., "Cellular mechanisms regulating epithelial morphogenesis and cancer invasion" Curr. Opin. Cell Biol., 22 (2010), pp. 640-650.

Gusterson, B., et al., "Basal cytokeratins and their relationship to the cellular origin and functional classification of breast cancer" Breast Cancer Res., 7 (2005), pp. 143-148.

Guy, C., et al., "Induction of mammary tumors by expression of polyomavirus middle T oncogene: a transgenic mouse model for metastatic disease" Mol. Cell. Biol., 12 (1992), pp. 954-961.

Guy, C., et al., "1992b Expression of the neu protooncogene in the mammary epithelium of transgenic mice induces metastatic disease" Proc. Natl. Acad. Sci. USA, 89 (1992), pp. 10578-10582.

Harris, J., et al., "Clinical dilemma of ductal carcinoma in situ" J Clin Oncol. Nov. 10, 2009;27(32):5303-5.

Herschkowitz, J., et al., "Identification of conserved gene expression features between murine mammary carcinoma models and human breast tumors" Genome Biol., 8 (2007), p. R76.

Kennecke, H., et al., "Metastatic behavior of breast cancer subtypes" J. Clin. Oncol., 28 (2010), pp. 3271-3277.

Kim, et al., "A keratin cytoskeletal protein regulates protein synthesis and epithelial cell growth" Nature, 441 (2006), pp. 362-365.

Korsching, E., et al., "Basal carcinoma of the breast revisited: an old entity with new interpretations" J Clin Pathol. May 2008;61(5):553-60.

Laakso, M., et al., "Basoluminal carcinoma: a new biologically and prognostically distinct entity between basal and luminal breast cancer" Clin. Cancer Res., 12 (2006), pp. 4185-4191.

Leighton, J., et al., "Pathogenesis of tumor invasion. II. Aggregate replication" Cancer Res., 20 (1960), pp. 575-586.

Lichtner, R., et al., "Coexpression of cytokeratins characteristic for myoepithelial and luminal cell lineages in rat 13762NF mammary adenocarcinoma tumors and their spontaneous metastases" Cancer Res., 51 (1991), pp. 5943-5950.

Lim, E., et al., "Aberrant luminal progenitors as the candidate target population for basal tumor development in BRCA1 mutation carriers" Nat. Med., 15 (2009), pp. 907-913.

Lin, E., et al., "Progression to malignancy in the polyoma middle T oncoprotein mouse breast cancer model provides a reliable model for human diseases" Am. J. Pathol., 163 (2003), pp. 2113-2126.

Madsen, C., et al., "Cancer dissemination—lessons from leukocytes" Dev Cell. 2010;19(1):13-26.

Malzahn, K., et al., "Biological and prognostic significance of stratified epithelial cytokeratins in infiltrating ductal breast carcinomas" Virchows Arch., 433 (1998), pp. 119-129.

Maroulakou, I., et.al, "Prostate and mammary adenocarcinoma in transgenic mice carrying a rat C3(1) simian virus 40 large tumor antigen fusion gene" Proc Natl Acad Sci (1994); 91(23): 11236-11240.

Martin, K., et.al, "Prognostic breast cancer signature identified from 3D culture model accurately predicts clinical outcome across independent datasets" PLos One 3(8): e2994.

Molyneux, G., et al., "BRCA1 basal-like breast cancers originate from luminal epithelial progenitors and not from basal stem cells" Cell Stem Cell, 7 (2010), pp. 403-417.

Moumen, M., et al., "The mammary myoepithelial cell" Int. J. Dev. Biol., 55 (2011), pp. 763-771.

Muzumdar, M., "A global double-fluorescent Cre reporter mouse" Genesis, 45 (2007), pp. 593-605.

Nelson, W., "Remodeling Epithelial Cell Organization: Transitions Between Front-Rear and Apical-Basal Polarity" Cold Spring Harb Perspect Biol. (2009); 1(1): a000513.

Neve, R., et al., "A collection of breast cancer cell lines for the study of functionally distinct cancer subtypes" Cancer Cell, 10 (2006), pp. 515-527.

Nguyen-Ngoc, K., et al. "ECM microenvironment regulates collective migration and local dissemination in normal and malignant mammary epithelium" Proc. Natl. Acad. Sci. USA, 109 (2012), pp. E2595-E2604.

Paszek, M., et al., "Tensional homeostasis and the malignant phenotype" Cancer Cell, 8 (2005), pp. 241-254.

Petrocca, F., et al., "A genome-wide siRNA screen identifies proteasome addiction as a vulnerability of basal-like triple-negative breast cancer cells" Cancer Cell, 24 (2013), pp. 182-196.

Polyak, K., et al., "Transitions between epithelial and mesenchymal states: acquisition of malignant and stem cell traits" Nat. Rev. Cancer, 9 (2009), pp. 265-273.

Polyak, K., "Molecular markers for the diagnosis and management of ductal carcinoma in situ" J. Natl. Cancer Inst. Monogr., 2010 (2010), pp. 210-213.

Proia, T., et al, Genetic predisposition directs breast cancer phenotype by dictating progenitor cell fate. Cell Stem Cell. (2011);8(2):149-63.

Provenzano, P., et al., Collagen density promotes mammary tumor initiation and progression. BMC Med., 6 (2008), p. 11.

Rakha, E., et al., Basal-like breast cancer: a critical review. J Clin Oncol. 2008; 26(15):2568-81.

Roussos, E., et.al., Chemotaxis in cancer. Nat Rev Cancer. 2011; 11(8): 573-87.

Sun, P., et al., Cytokeratin expression during mouse embryonic and early postnatal mammary gland development. Histochem. Cell Biol., 133 (2010), pp. 213-221.

Vaezi, A., et al.,Actin cable dynamics and Rho/Rock orchestrate a polarized cytoskeletal architecture in the early steps of assembling a stratified epithelium. Dev. Cell, 3 (2002), pp. 367-381.

Voduc, K., et.al., Breast cancer subtypes and the risk of local and regional relapse. J Clin Oncol. Apr. 1, 2010;28 (10):1684-91. doi: 10.1200/JCO.2009.24.9284. Epub Mar. 1, 2010.

Weber, G., et al., A mechanoresponsive cadherin-keratin complex directs polarized protrusive behavior and collective cell migration. Dev. Cell, 22 (2012), pp. 104-115.

Weigelt, B., et al., Unraveling the microenvironmental influences on the normal mammary gland and breast cancer. Semin. Cancer Biol., 18 (2008), pp. 311-321.

Wolf, K., et al., Collagen-based cell migration models in vitro and in vivo. Semin. Cell Dev. Biol., 20 (2009), pp. 931-941.

Wyckoff, J., A critical step in metastasis: in vivo analysis of intravasation at the primary tumor. Cancer Res. May 1, 2000;60(9):2504-11.

Wyckoff, J., et.al, Direct visualization of macrophage-assisted tumor cell intravasation in mammary tumors. Cancer Res. Mar. 15, 2007;67(6):2649-56.

Yamada, S., et al., Pairwise assembly determines the intrinsic potential for self-organization and mechanical properties of keratin filaments. Mol. Biol. Cell, 13 (2002), pp. 382-391.

Pavelic, K., et al., "Growth of human urological tumors on extracellular matrix as a model for the in vitro cultivation of primary human tumor explants" Cancer Research (1986) vol. 46, pp. 3653-3662.

(56) References Cited

OTHER PUBLICATIONS

Slocum, H., et al., "Characterization of cells obtained by mechanical and enzymatic means from human melanoma, sarcoma, and lung tumors" Cancer Research (1981) vol. 41, pp. 1428-1434.

* cited by examiner

MOLECULAR SIGNATURES OF INVASIVE CANCER SUBPOPULATIONS

CROSS-REFERENCE TO RELATED APPLICATIONS

This application claims the benefit of U.S. Provisional Application No. 61/915,050, filed Dec. 12, 2013, and U.S. Provisional Application No. 61/822,713, filed May 13, 2013, each of which are incorporated herein by reference in their entireties.

STATEMENT OF GOVERNMENTAL INTEREST

This invention was made with government support under grant no. CA103175, CA088843, CA155758, and W81XWH-12-1-0018 awarded by the National Institutes of Health and the ARMY/MRMC. The government has certain rights in the invention.

FIELD OF THE INVENTION

The present invention relates to the field of cancer. More specifically, the present invention provides assays for identifying molecular signatures of invasive cancer subpopulations.

BACKGROUND OF THE INVENTION

The large majority of cancers in the United States initiate from epithelial cells. In these epithelial cancers the major clinical problem is metastasis. A major unsolved challenge is determining which of the many cell epithelial cell types are most important to the tumor's ability to invade, metastasize, and resist therapy. Most efforts to classify the relative ability of cancer cells to initiate tumors or to metastasize to distant sites rely on sorting the cells based on cell surface markers prior to analysis. The sorting can be accomplished by Fluorescence Activated Cell Sorting (FACS) or by Magnetic Activated Cell Sorting (MACS). However, in either case the researcher needs to decide in advance how to identify the cell population to be tested and cell populations can only be compared that both survive the sorting process and for which reliable cell surface markers or other fluorescent reporters can be developed. Accordingly, these approaches may fail to identify the cancer cell subpopulations that are actually driving the functional properties of the tumor.

SUMMARY OF THE INVENTION

Epithelial tumors are heterogeneous and contain many different epithelial and stromal cell populations. Work in recent years has focused on identifying stromal cell populations in the tumor microenvironment that can modify the invasive, metastatic or therapeutic resistance properties of the tumor. Comparatively less is known about the different epithelial populations within solid tumors. The present invention is based, at least in part, on the development of techniques for isolating tissue from primary tumors for live culture while retaining the natural diversity of epithelial cell types. We have further developed assays that enable stratification of the cancers cells based on their invasive behavior. Importantly, the stratification is prospective and we do not require a priori molecular knowledge, or cell surface marker-based sorting, of the epithelial populations in advance of the invasion assays. We have both developed techniques to prospectively identify the most invasive cells in a solid tumor and we have also developed specific molecular signatures for invasive subpopulations based on work in multiple mouse models of mammary carcinoma.

We have developed protocols to identify the most invasive populations within epithelial tumors using 3D culture techniques that establish a competitive invasion and metastasis assay within 2D or 3D microenvironments composed of extracellular matrix proteins. We have extensively evaluated our assay in a mouse model of mammary carcinoma and have used it to identify a novel and rare (~10% of epithelial cells) cell populations that robustly leads invasion in 3D culture, is positioned at the front of invasive strands in vivo, is the dominant cell type in lung micrometastases, and appears to be more resistant to therapy. We have therefore both developed a general approach for prospectively identifying the most invasive epithelial cell populations within a tumor and have developed a novel molecular signature for a specific subpopulation (keratin-14+, p63+, P-cadherin+, smooth muscle alpha actin−). We have then used the molecular signature we developed to identify this novel subpopulation in each of three additional mouse mammary carcinoma models we have tested. Importantly, this novel highly invasive subpopulation is present in both luminal and basal mammary carcinomas suggesting it may be a therapeutically important cell type in multiple subtypes of human breast cancer.

In preliminary experiments this novel basal cell population is also more resistant to therapy than the bulk K14− cells in the tumor. Combined with the overrepresentation of these novel basal cells in lung micrometastases, our data suggest that the most invasive cell population in our assay predicts the molecular features of distributed lung metastases. A major clinical problem in epithelial cancers is developing treatment regimens capable of eliminating distributed micrometastases, many of which will be undetectable at the time of adjuvant chemotherapy. Knowing the molecular characteristics of this population could aid in designing personalized treatment regimens for individual patients that are more likely to achieve curative results. Since it is typically not possible to sample directly the micrometastatic sites in a patient our assays enable isolation of a surrogate for these sites based on much more readily available tissue from the primary tumor.

Our assays: (1) enable efficient live culture of primary tumor tissue with retention of the varied epithelial cell types; (2) enable prospective identification of the most invasive epithelial cell populations without requiring prior knowledge of the cells' molecular characteristics; and (3) enable ready recovery of the most invasive cell populations for molecular characterization. In addition, we can collect thousands of epithelial fragments per tumor and so can work in parallel to identify the invasive subpopulations, determine their relative abundance, and test their sensitivity to different chemotherapies. Finally, our assay has been optimized for multiwell plate format.

Accordingly, in one aspect, the present invention provides methods for characterizing invasive cells within tumors. In one embodiment, a method for characterizing invasive cells within primary tumors comprises the steps of (a) isolating primary tumors from a subject; (b) generating tumor organoids via mechanical disruption and/or enzymatic digestion; (c) culturing tumor organoids in an extracellular matrix gel; and (d) determining the molecular phenotype of the cells leading the invasive strands of the cultured tumor organoids using gene expression profiling. In certain embodiments, the extracellular matrix gel is a collagen I gel.

In particular embodiments, the extracellular matrix gel is a three-dimensional extracellular matrix gel.

In another aspect, the present invention provides methods for treating cancer patients. In one embodiment, a method for treating a patient having a primary tumor comprises the steps of (a) isolating tissue from the patient's tumor; (b) culturing the tissue in an extracellular matrix gel; (c) determining the molecular phenotype of the cells leading the invasive strands of the cultured tumor organoids using gene expression profiling; and (e) treating the patient based on the identity of the molecular phenotype of the invasive cells. In a specific embodiment, the extracellular matrix gel is a collagen I gel. In particular embodiments, the extracellular matrix gel is a three-dimensional extracellular matrix gel. In another embodiment, a method for treating a patient having a tumor comprising basal leader cells comprises the step of administering to the patient an agent that inhibits keratin 14 and/or p63.

In a further embodiment, a method for treating a patient having a primary tumor comprises the steps of (a) isolating tissue from the patient's tumor; (b) culturing the tissue in an extracellular matrix gel; (c) determining the molecular phenotype of the cells leading the invasive strands of the cultured tumor organoids using gene expression profiling; and (d) testing the invasive cells using one or more cancer treatments; and (e) treating the patient based on the cancer treatment that shows the best success rate in step (d). In particular embodiments, the extracellular matrix gel is a three-dimensional extracellular matrix gel.

The present invention also provides methods for estimating the likelihood of distant metastases of a primary tumor in a patient comprising the steps of (a) isolating tissue from the patient's tumor; (b) culturing the tissue in an extracellular matrix gel; and (c) estimating the likelihood and/or rate of metastatic spread based on the frequency of invasion in the cell culture. In a specific embodiment, the extracellular matrix gel is a collagen I gel. In particular embodiments, the extracellular matrix gel is a three-dimensional extracellular matrix gel.

In yet another aspect, the present invention provides methods for identifying subpopulations of cells. In one embodiment, a method for identifying invasive subpopulations in sections from fixed tissue from archival human tumor sections comprises the step of staining for a basal leader signature comprising keratin 14+, p63+, P-cadherin+, and smooth muscle actin–. In another embodiment, a method for identifying invasive subpopulations in sections from fixed tissue from archival human tumor sections comprises analyzing mRNA expression signatures for a basal leader signature comprising keratin 14+, p63+, P-cadherin+, and smooth muscle actin–. In other embodiments, the signature comprises K14+. In certain embodiments, the signature further comprises one or more of, p63+, P-cadherin+, and smooth muscle actin–. In a specific embodiment, the tumor is a carcinoma. In other embodiments, the carcinoma is basal cell carcinoma, squamous cell carcinoma, renal cell carcinoma, ductal carcinoma in situ, invasive ductal carcinoma, or adenocarcinoma. The adenocarcinoma can be include, but is not limited to, breast, hepatocellular, prostate, colon and lung.

n=22-70 tumor organoids per mouse model. (E) Frequency of leader cells expressing K14 or SMA in MMTV-Neu or C3(1)/Tag tumor organoids. 95% confidence intervals for each proportion denoted in parentheses. (F) Time-lapse DIC microscopy of a human lumenal breast tumor organoid embedded in collagen I matrix (sample 11). White bar, leader cell. At right, micrograph of tumor organoid from same tumor specimen, stained for K14, SMA, and F-actin. See also Movie 10 (not shown). (G) Pathologic characteristics of harvested human breast tumors, including stage, grade, ER status, PR status, HER2/Neu status, Ki-67 percentage, and the measured frequency of K14+ leaders. 9 of 10 tumors were ER-positive lumenal breast tumors, with ER positivity ranging from 20%-100%. The breast cancer subtype was determined using surrogate immunohistochemistry definitions (Goldhirsch et al., 2013). (H) Representative micrograph of a K14+ collective invasion front from an archival specimen classified as lumenal B. (I) The distribution of cases according to breast cancer subtype assigned using surrogate IHC subtype definitions. n=39 cases in total. (J) The frequency of cases with low (+), medium (++), or high (+++) K14 staining stratified by IHC-defined breast cancer subtype. K14 intensity was scored as in FIG. 11A. (K) The distribution of cases according to histologic tumor grade. (L) The frequency of cases with low (+), medium (++), or high (+++) K14 staining stratified by tumor grade. Scale bar, 50 mm in (A and F) (left movie series), 20 mm in (B and F) (right panel), and 100 mm in (H). See also FIGS. 10 and 11.

Figure 4:
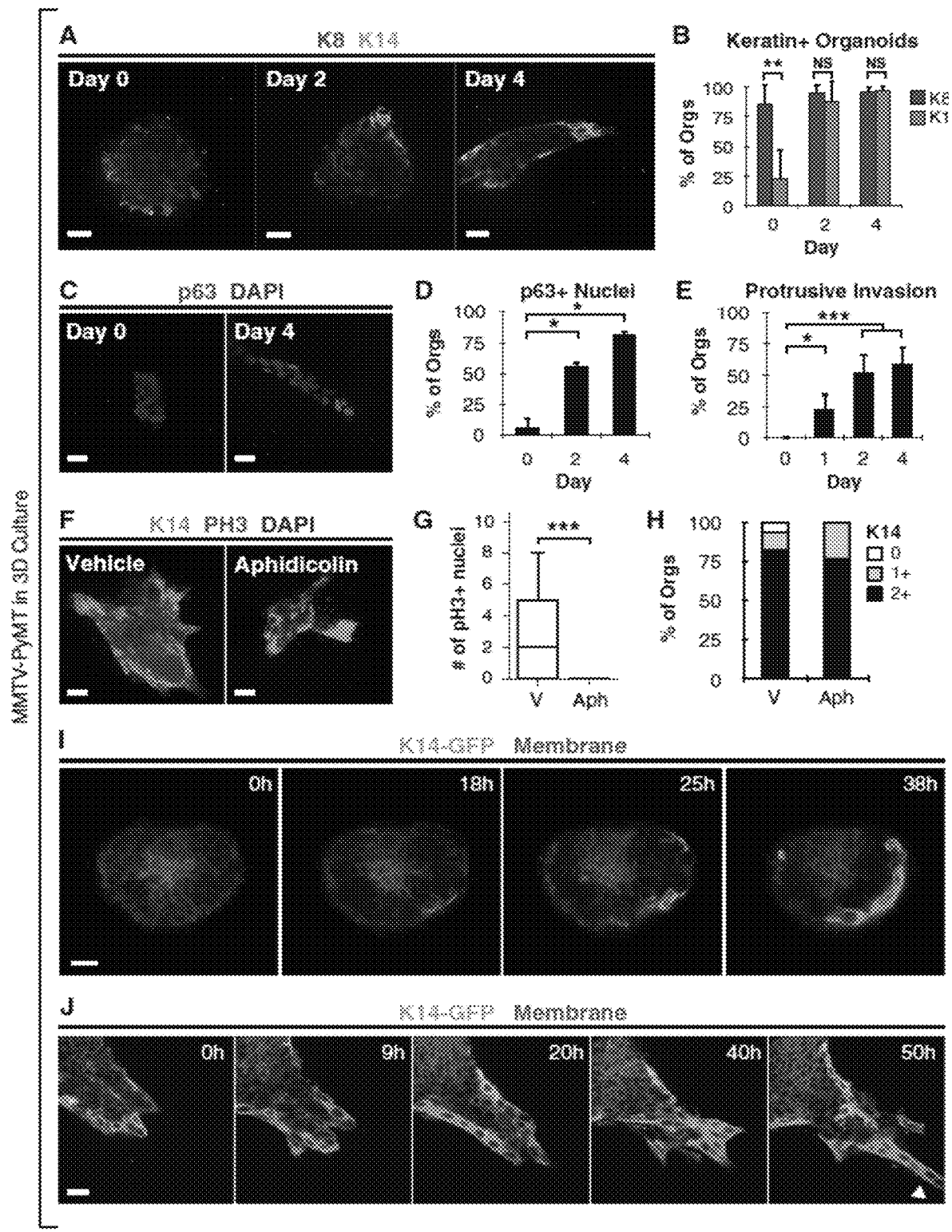

FIG. 4. Lumenal Tumor Cells Acquire Markers of Basal Differentiation (A) Mouse mammary tumor organoids grown in 3D collagen matrix stained with K8 and K14. (B) Bar graph of percentage of tumor organoids with K8 or K14 intensity equal to or greater than 1+ as a function of time. K14 and K8 intensity was quantified into 0 (no or few), 1 (intermediate), or 2 (bright) K14 signal. Data are presented as mean±SD. For K14: n=719 organoids from 5-8 mice per day; for K8: n=269 organoids from 3 mice per day. (C) Mammary tumor organoids grown in 3D collagen matrix stained with p63 and DAPI. (D) The percentage of organoids with nuclei positive for p63 was counted. Data are presented as mean±SD. n=114 organoids from 2 mice per day. (E) Invasion was quantified by scoring protrusive morphology of cancer cells in contact with the ECM. Data are presented as mean±SD. n=916 organoids from 4-7 mice per day. (F) Tumor organoids treated from day 0 with DMSO vehicle or a mitosis inhibitor (aphidicolin 10 mM) stained with K14, pH3, and DAPI. (G) The number of pH3+ nuclei per tumor organoid in vehicle or mitosis inhibitor (aphidicolin)-treated conditions. Data are presented as boxplots. n=79 organoids from 2 mice per condition. (H) K14 intensity scored in vehicle or aphidicolin. K14 intensity was quantified into 0 (no or few), 1 (intermediate), or 2 (bright) K14 signal. n=110 organoids from 2 mice per condition. (I) Time-lapse microscopy of MMTV-PyMT tumor organoids expressing GFP under the control of the K14 promoter (K14-GFP), beginning at the start of culture. See also Movie 11 (not shown). (J) K14-GFP+ cells migrate collectively and lead trailing K14-GFP− cells. Arrowhead, K14+ leader cell invasion. See Movie 11 (not shown). All p values were determined by two-sided t test. *p<0.05. p<0.01. *p<0.001. Scale bars, 40 mm in (F) and 20 mm in (A, C, I, and J). See also FIG. 12.

Figure 5:
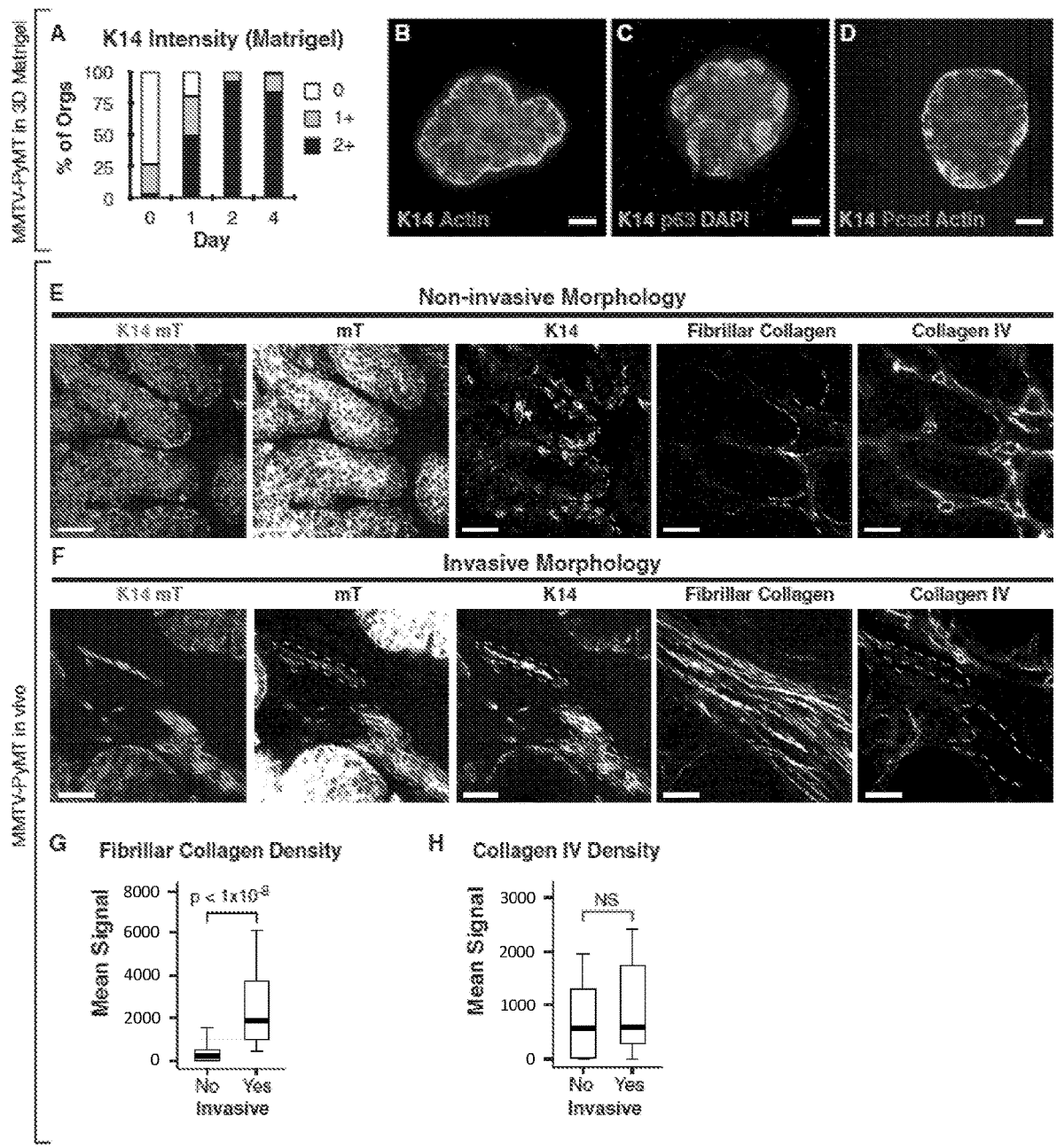

FIG. 5. K14+ Cells Acquire Leader Cell Behaviors Specifically in Collagen-I-Rich Local Microenvironments (A) K14 intensity of tumor organoids grown in 3D Matrigel. K14 intensity was quantified into 0 (no or few), 1 (intermediate), or 2 (bright) K14 signal. n=471 organoids, 3-5 tumors per day. (B-D) Micrographs of tumor organoids cultured in 3D Matrigel stained with K14 and phalloidin (B), K14, p63, and DAPI (C) or K14, P-cadherin, and phalloidin (D). (E and F) Thick sections from in vivo primary MMTV-PyMT tumor were stained for K14 and collagen type IV and were assayed for fibrillar collagen by SHG. Regions with K14+ cells were identified and classified as having either noninvasive or invasive morphology. Noninvasive morphology was defined as K14+ cells with smooth membrane borders (E, leftmost panel). Invasive morphology was defined as protrusive strands of K14+ cells (F, leftmost panel). The same sections were assayed for fibrillar collagen (second panels from right) and for collagen IV (rightmost panels). Red hash marks outline the border of noninvasive (E) and invasive structures (F). (G and H). The correlation of invasive morphology of K14+ cells with the abundance of fibrillar collagen or collagen IV density in vivo in MMTV-PyMT tumors. Data are presented as boxplots. n=37-53 sections per condition across 8 mice. p values were determined by two-sided t test. Scale bars, 20 mm in (B-D) and 40 mm in (E and F). See also FIG. 13.

Figure 6:
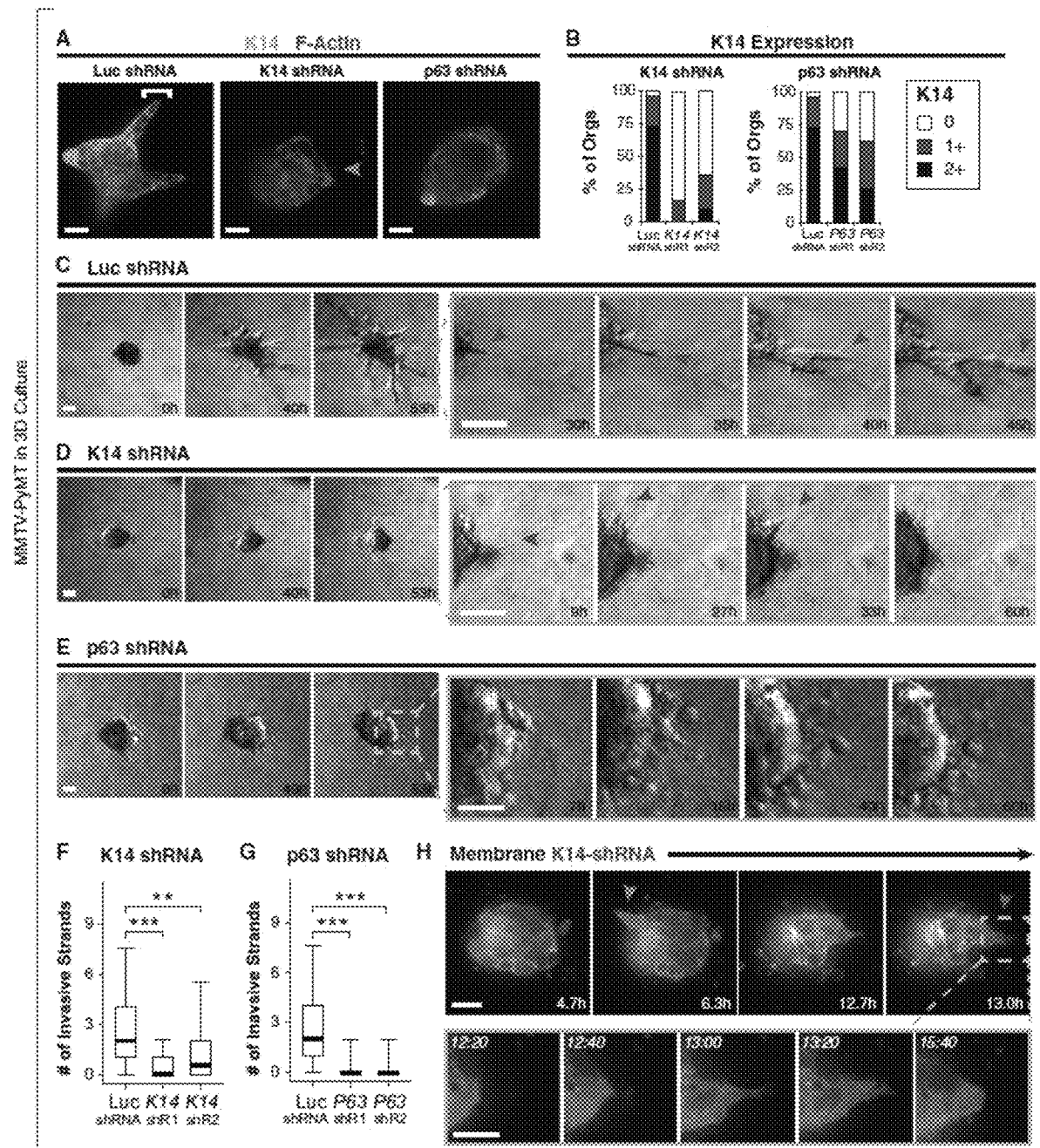

FIG. 6. Basal Epithelial Genes K14 and p63 Are Required for Collective Invasion in 3D Culture (A) Micrographs of MMTV-PyMT tumor organoids transduced with lentiviral particles encoding shRNAs against luciferase control (Luc shRNA), K14 (K14 shRNA), or p63 (p63 shRNA) and then embedded in collagen I matrix and stained for K14 and Phalloidin. Left: bracket, leader cell. Middle: blue arrow, K14− protrusive cell. (B) K14 intensity was quantified into 0 (no or few), 1 (intermediate), or 2 (bright) K14 signal for organoids from (A). n=61-93 organoids per condition from 3 independent experiments. (C-E) Time-lapse DIC microscopy of transduced organoids as in (A). In Luc shRNA transduced organoids, the tumor organoid invades collectively (C). Inset shows protrusive cells that extend and expand into a collective invasive strand. In K14 shRNA transduced organoids, tumor organoids do not invade collectively (D). Inset shows that protrusive behavior is intact. In p63 shRNA transduced organoids, tumor organoids do not invade collectively (E). Inset shows lack of protrusions and rounded cell borders in p63-kd1 tumor organoids. See Movie 14 (not shown). (F and G) The number of collective invasive strands in Luc shRNA, K14-shRNA kd1 and kd2, and p63-shRNA kd1 and kd2 transduced organoids was determined from time-lapse movies. The maximal number of invasive strands at any time was determined. n=170 movies for Luc shRNA from 7 independent experiments. n=133 movies for K14 shRNA kd1 from 7 independent experiments. n=36 movies for K14 shRNA kd2 from 3 independent experiments. n=90 movies for p63 shRNA kd1 from 5 independent experiments. n=42 movies for p63 shRNA kd2 from 3 independent experiments. Data are presented as boxplots. p values were determined by two-sided t test. p<0.001. *p<1×10-10. (H) Time-lapse sequence of a representative tumor organoid transduced with lentiviral particles encoding for dual expression of K14-shRNA and GFP. GFP is shown in false color purple. Arrows, individual GFP+(and K14-shRNA-expressing) protrusive cells. Scale bars, 20 mm in (A), 50 mm in (C-E), and 10 mm in (H). See also FIG. 14.

Figure 2:
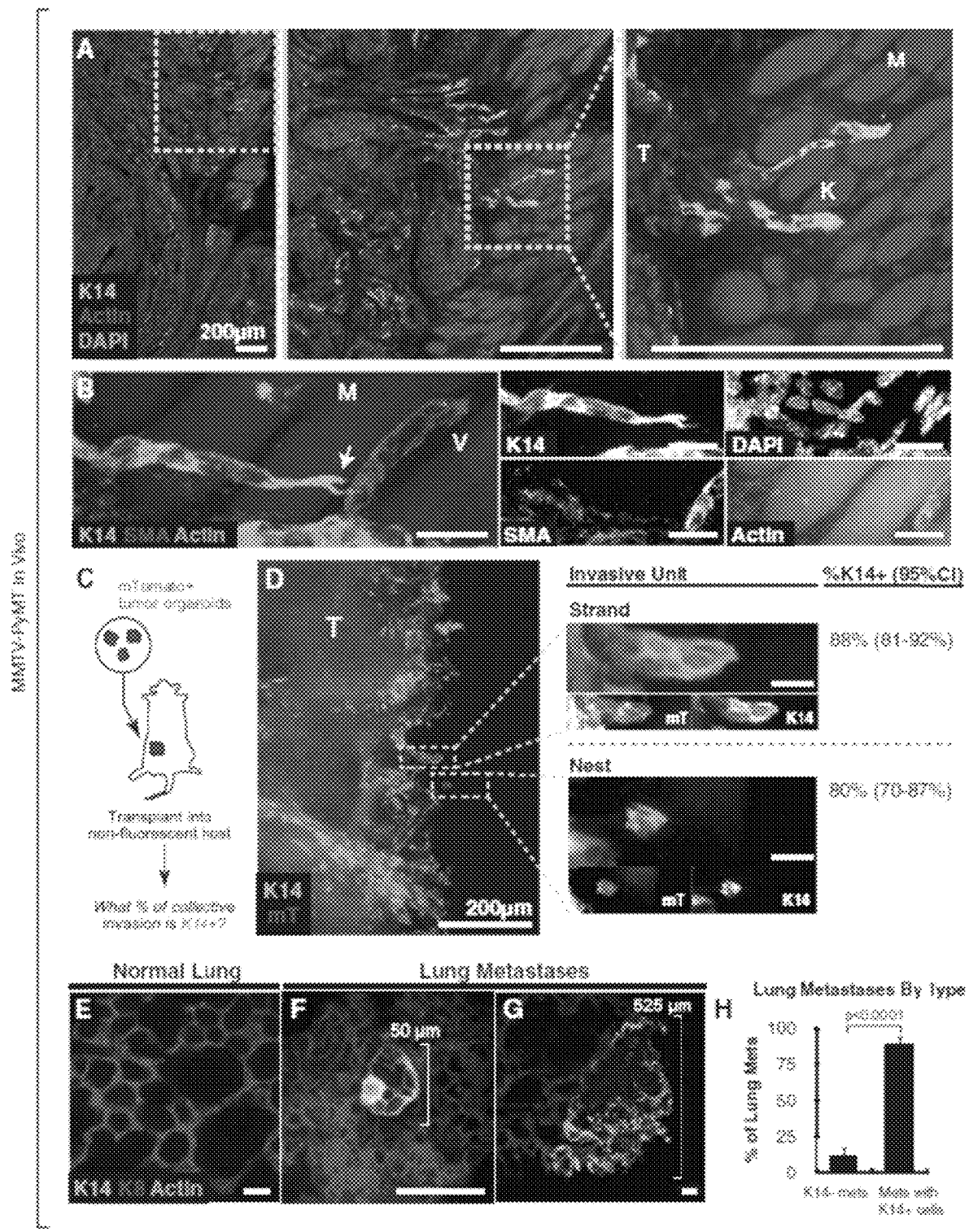
FIG. 2. K14+ Cells Are Enriched at the Tumor Invasive Border and in Lung Metastases (A) Area of tumor invasion into muscle in 100-mm thick mammary tumor sections, stained with K14, DAPI, and phalloidin. T, tumor; K, K14+ leader cells; M, phalloidin+ muscle fibers. (B) Collectively invading K14+ leaders at high magnification stained with K14, phalloidin, SMA, and DAPI. M, muscle; V, SMA+ vessel; arrow, leading K14+ cell with forked protrusions. Inset highlights the chain of three K14+ cells. This micrograph represents a z-projection of more than 40 mm to capture the organization of the invasive strand. See Movie 9 (not shown). (C) Schema to quantify the percentage of collective invasion that is led by K14+ cells. mTomato+ tumor organoids were isolated from MMTV-PyMT; mT/mG mice. Organoids were transplanted orthotopically into non-fluorescent congenic hosts. Transplanted tumors >1 cm in size were harvested to generate montages of the tumor-stromal border. (D) Micrograph of a representative mTomato+ tumor-stromal border stained with K14. mTomato+ regions (in red) denote tumor-derived cells. Insets denote multicellular groups of cells invading into the adjacent stroma. An invasive strand was defined as a protrusive group of cells connected to the main tumor. A nest was defined as an isolated group of tumor cells. n=145 invasive strands and n=83 nests were counted from 13 sections from 5 mice. 95% confidence intervals denoted in parentheses. The micrograph represents a 40 mm z-projection. (E-G) Reconstructed metastases inthick sections of lungs from MMTV-PyMT mice, stained with K14, K8, and phalloidin. Normal lung parenchyma was K14 negative (E). Both micrometastatic and larger metastatic lesions had K14+ and K8+ cells (F and G). (H) Metastatic lung lesions were identified by K8 positivity and were classified based on their K14 status. Data are presented as mean±SD. n=226 metastases from 5 tumor mice. p value was determined by two-sided t test. Scale bars, 20 mm in (B and D) and 50 mm in (E-G). See also FIG. 9.
Figure 7:
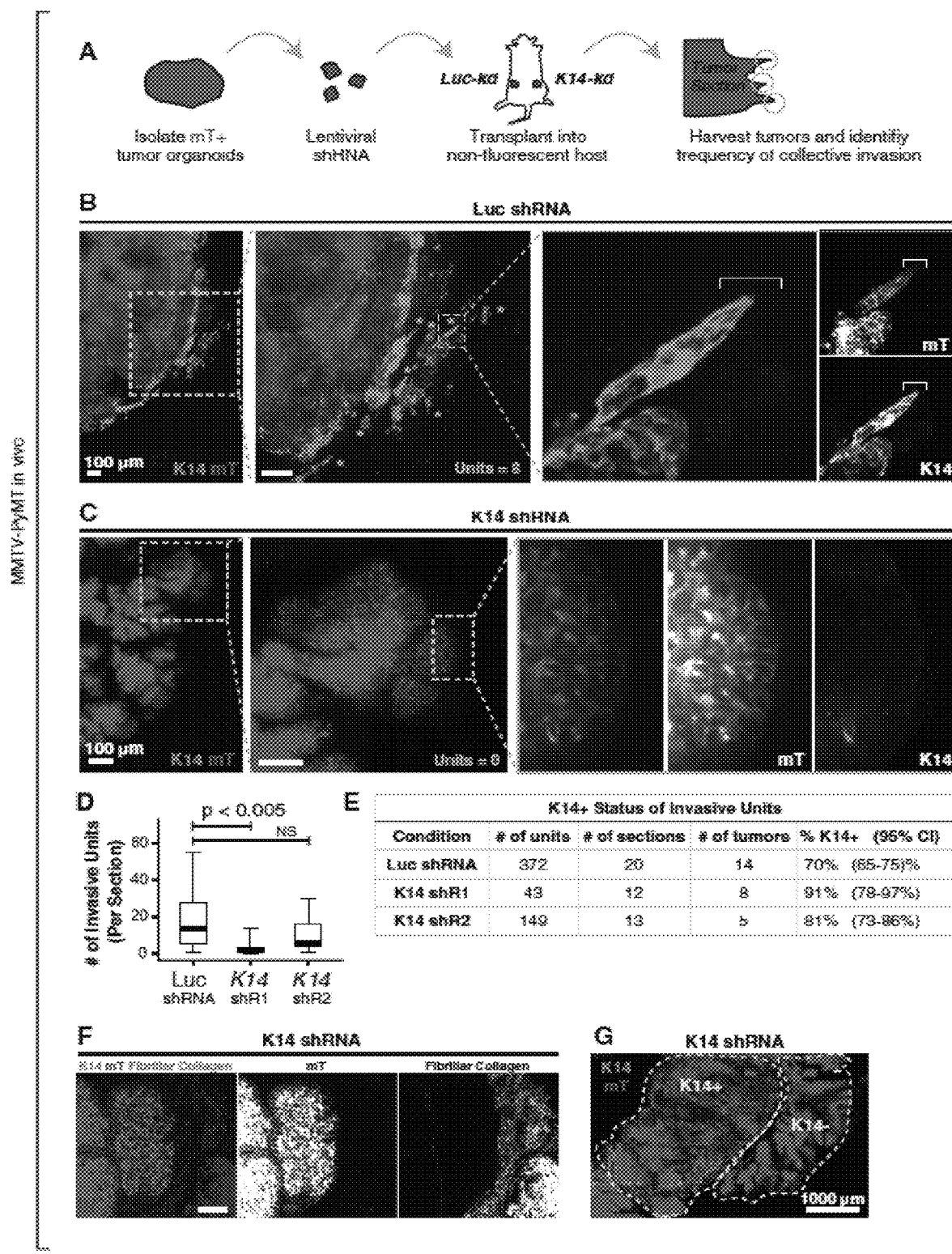

FIG. 7. In Vivo Knockdown of K14 Disrupts Collective Invasion at the Tumor-Stromal Border (A) Schema to test the in vivo requirement for K14 in collective invasion. Fluorescent mTomato+(mT+) tumor organoids were transduced with either Luc shRNA (Luc-kd) or K14-shRNA (K14− kd), selected with puromycin, and transplanted into the cleared mammary fat pads of nonfluorescent congenic FVB hosts. Tumor was isolated at ~1 cm, and montages of the tumor-stromal border were assembled. (B) Micrograph of the tumor-stromal border from a representative Luc-kd tumor stained with K14. mT+ regions (in red), tumor-derived cells. Insets, collective invasive units in the Luc-kd tumor. The micrograph represents a z-projection of more than 40 mm. (C) Micrograph of the tumor-stromal border from a representative K14-kd1 tumor stained with K14. mT+ regions (in red), tumor-derived cells. Insets, representative K14− noninvasive border. (D) Median number of invasive units per section in Luc-kd and K14-kd tumors, with data presented as a boxplot. Invasive units included strands and nests as described in FIG. 2E. p values were determined by two-sided t test. (E) Frequency of invasive units expressing K14 in Luc-kd and K14-kd tumor sections. 95% confidence intervals for each proportion were denoted in parentheses. (F) Representative micrograph of K14-kd1 tumorstromal border stained for K14 and assayed for fibrillar collagen by SHG. mT+ regions (in red), tumor-derived cells. (G) Micrograph of a K14-kd1 tumor stained with K14, demonstrating K14+ and K14− tumor foci. The micrograph represents a z-projection of more than 40 mm. Scale bars represent 100 mmin (B and C), 40 mm in (F), and 1,000 mm in (G).

Figure 1:
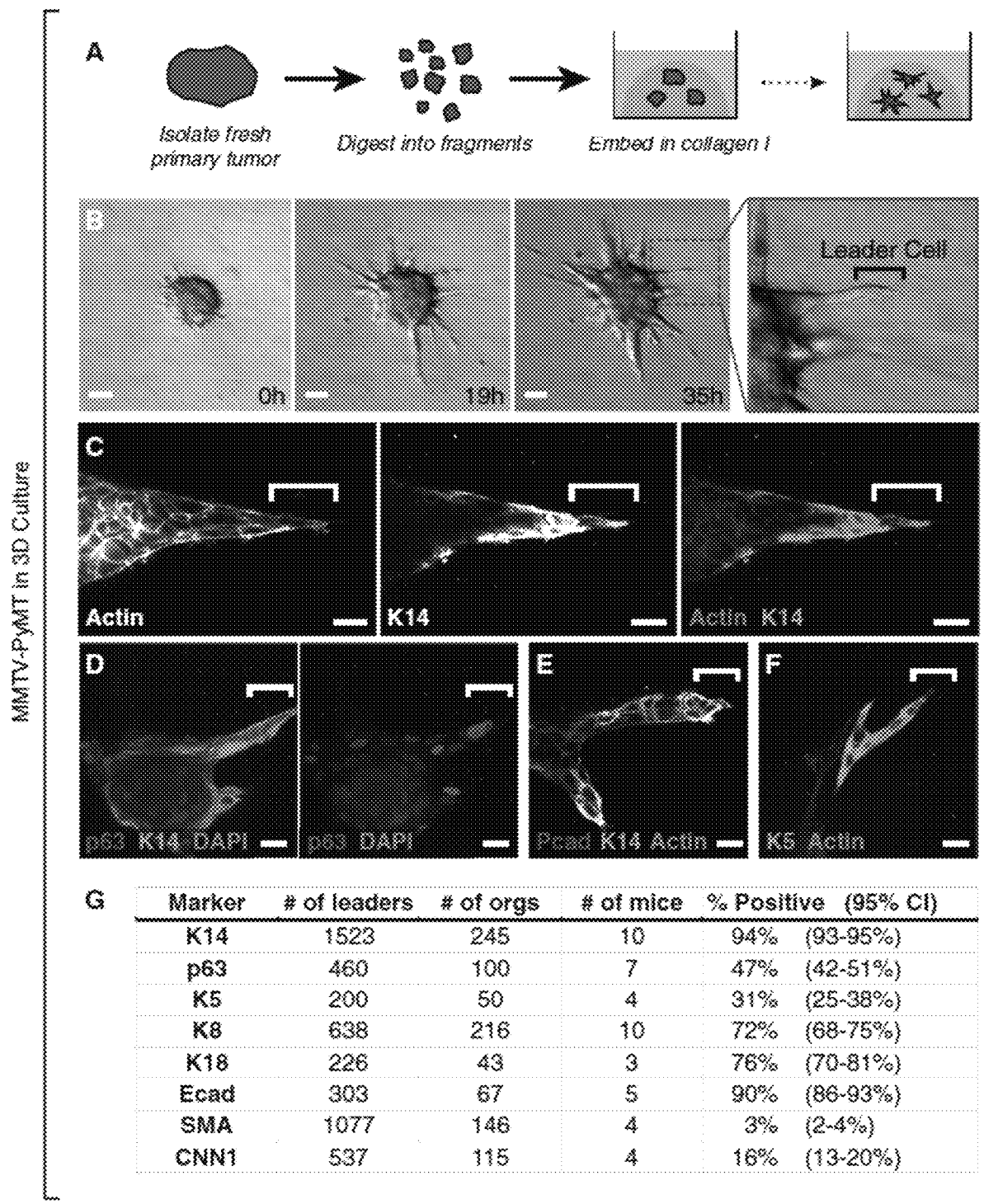
FIG. 1. Leaders Cells Are Molecularly Distinct and Express Basal Epithelial Markers in a Lumenal Mammary Carcinoma Model (A) Schema of a leader cell assay. The primary tumor is digested to tumor organoids, each composed of 200-1,000 adherent tumor cells, and embedded in 3D collagen I matrix. (B) Time-lapse DIC microscopy of a MMTV-PyMT mouse mammary tumor organoid embedded in collagen I. Collectively migrating cells emerge from the tumor organoid. Protrusive leader cells are readily identified at the front of these invasive strands. See also Movie 8 (not shown). (C-F) Leader cells stained with K14 and phalloidin (C), p63, K14 and DAPI (D), P-cadherin (Pcad), K14, and phalloidin (E) or K5 and phalloidin (F). (G) Frequency of leader cells expressing K14, p63, K5, K8, K18, E-cadherin (Ecad), SMA, and CNN1 in MMTV-PyMT tumor organoids. 95% confidence intervals for each proportion are denoted in parentheses. Scale bars, 50 mm in (B) and 20 mm in (C-F). See also FIG. 8.
Figure 8:
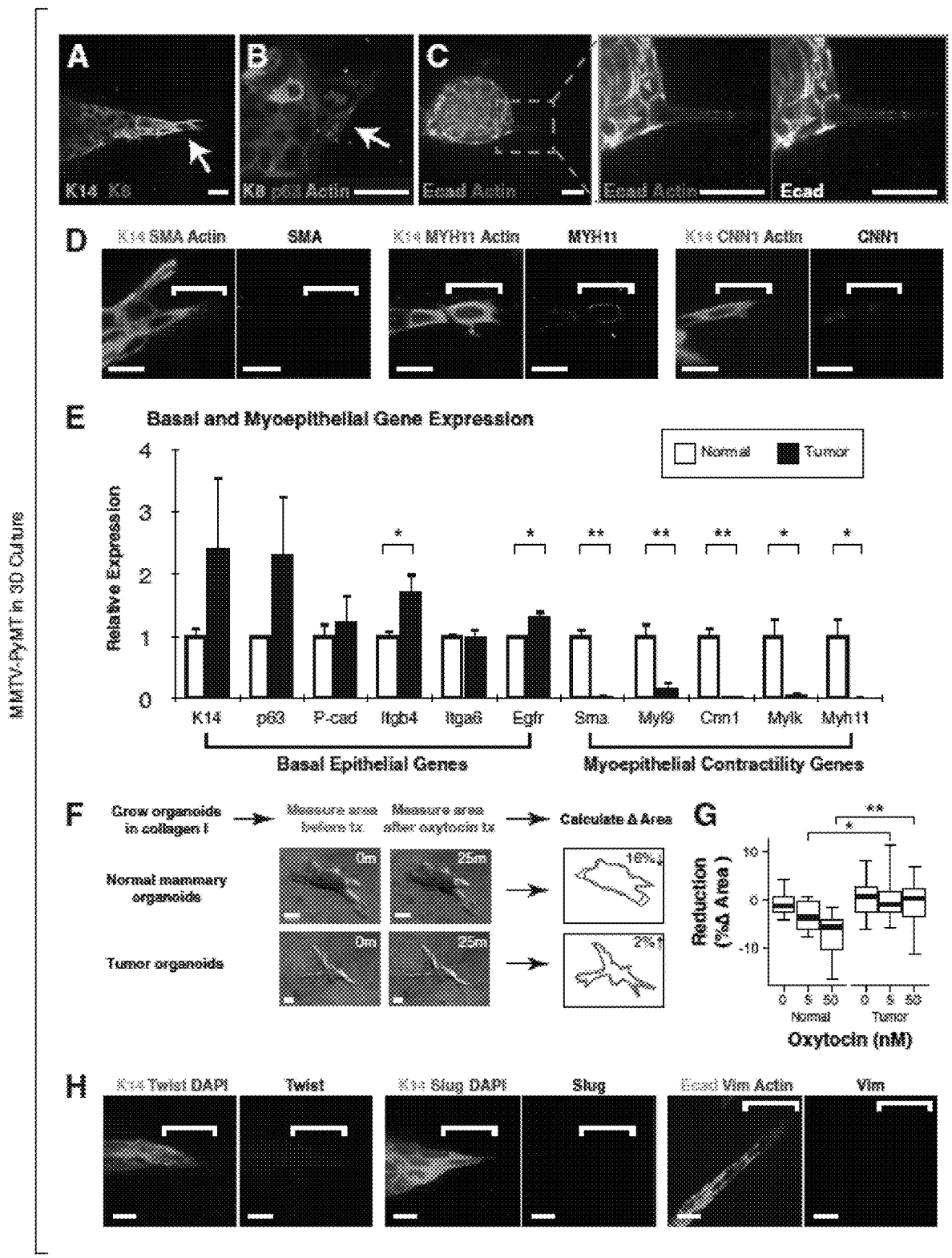

FIG. 8. Leader Cells Are Molecularly Distinct from Normal Differentiated Myoepithelial Cells and Coexpress Lumenal Epithelial Markers, Related to FIG. 1 (A-C) Leader cells from MMTV-PyMT tumor organoids stained with K14 and K8 (A), K8, p63, and phalloidin (B), or E-cadherin (Ecad) and phalloidin (C). Arrow in (A), a K14+K8+ cell. Arrow in (B), a K8+p63+ cell. 75% of leaders were K14+K8+(n=21/28) and 34% of leaders were K8+p63+(n=22/65). Blue arrows in (C), Ecadherin staining at cell-cell contacts between leader and follower cells. (D) Leader cells from MMTV-PyMT tumor organoids were stained with K14, SMA, and phalloidin (left), K14, MYH11, and phalloidin (middle), and K14, CNN1, and phalloidin (right). (E) mRNA gene expression of core basal/myoepithelial genes between normal and tumor organoids grown in collagen I matrix for 4 days. Core genes were divided into basal epithelial genes and those specific to the myoepithelial contractility program. Data presented as mean±sd. n=3 normal and tumor organoids. **p<0.01, *p<0.05; p values determined by two-sided t test. (F) Schema of oxytocin contractility experiment. Normal mammary organoids and MMTV-PyMT tumor organoids were imaged by DIC microscopy and treated with oxytocin at nM concentrations. Maximal contraction was observed at 25 min postincubation. (G) The reduction in organoid area calculated in (F) provides a proxy for oxytocin-dependent contractility. Organoids were incubated in oxytocin at the specified doses, and the change in area was determined. Data are presented as box plots. N=23-30 organoids per condition from 3 independent experiments. *p<0.005, **p<13 $10^{a}$-4; p values determined by two-sided t test. (H) Leader cells from MMTV-PyMT tumor organoids were stained with K14, Twist, and DAPI (left), K14, Slug, and DAPI (middle), or E-cadherin (Ecad), Vimentin (Vim), and phalloidin (right). The scale bars represent 50 mm in (F), 20 mm in (A-C), and 10 mm in (D,H).

Figure 9:
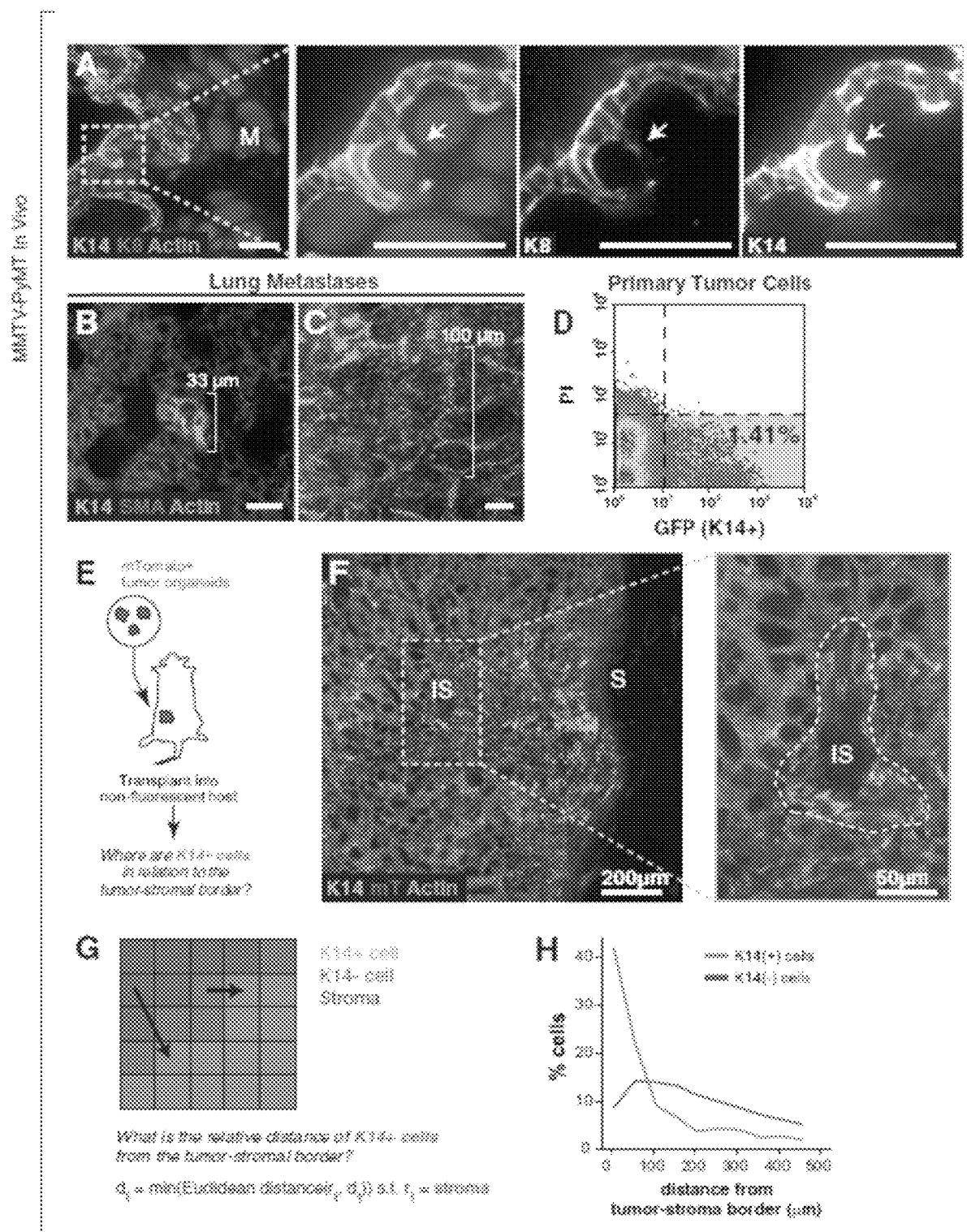

FIG. 9. K14+ Cells Are Enriched at the Tumor Invasive Border and in Lung Metastases, Related to FIG. 2 (A) Area of tumor invasion into muscle, stained with K14, K8, and phalloidin. Insert highlights a group of K14+K8+ cells. Arrow, protrusive tip of a K14+K8+ cell; M, F-actin+ muscle fibers. (B and C) Micrographs of reconstructed metastatic lung lesions stained with K14, SMA, and phalloidin. Both K14+ micrometastatic (B) and large lesions (C) are negative for SMA. (D) MMTV-PyMT mammary tumor that express GFP driven by the K14 promoter were dissociated and counted by FACS. Representative FACS plot (n=3 independent experiments). (E) Schema to determine the enrichment for K14+ cells at the tumor-stromal border. mTomato+ tumor organoids were transplanted orthotopically into nonfluorescent congenic hosts. Transplanted tumors >1 cm were harvested to generate montages of the tumor-stromal border. (F) Micrographs of a representative mTomato+ tumor-stromal border stained with K14 and phalloidin. (S), a tumor-stromal interface at the outside edge of the tumor. (IS), an "internal" region of tumor revealed by mTomato fluorescence to be a tumor-stromal interface. (G) Schema to quantify the frequency of K14+ cells relative to distance from the tumor-stromal interface. A Euclidian distance map was calculated, such that the distance to the nearest stromal pixel (defined as an mT−, F-actin+ pixel) was determined for each K14+ and K14− pixel. N=5 reconstructions from 4 tumors. (H) Frequency plot of the percentage of K14+ and K14− cells that are located as a function of distance from the tumor-stromal border, calculated from (G). Cell counts were pooled into 50 mm bins. The scale bars represent 20 mm in (A-C) and 500 mm in (F).

Figure 3:
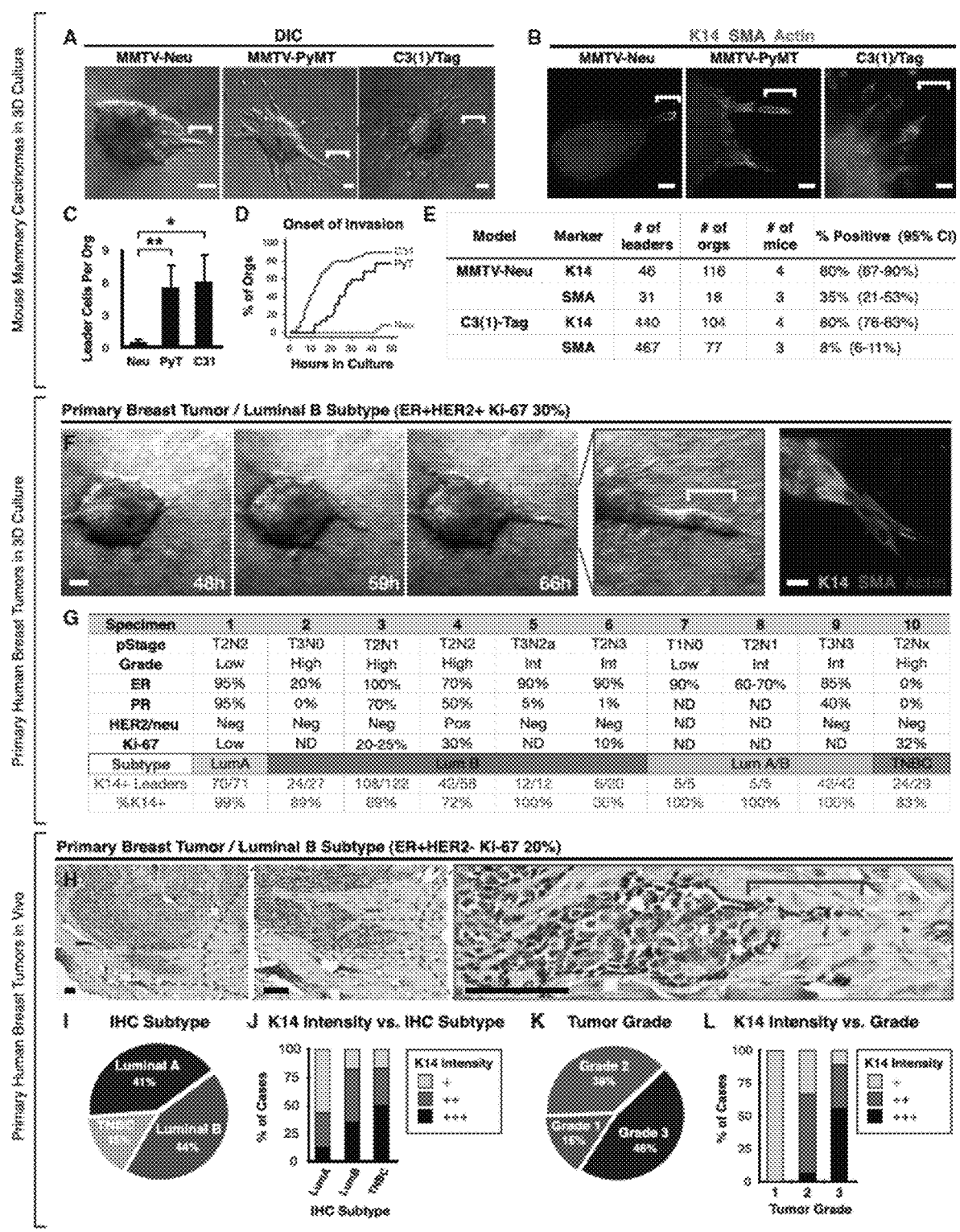
FIG. 3. K14+ Cells Lead Collective Invasion across Mouse Models of Breast Cancer and in Primary Human Breast Cancers (A) Time-lapse DIC microscopy of collagen-I-embedded organoids derived from MMTV-Neu, MMTV-PyMT, or C3(1)/Tag mammary tumors. White bars, leader cells. See also Movie 10 (not shown). (B) Micrographs of leader cells from the three mouse models in (A) stained with K14, SMA, and phalloidin. (C) Quantification of the number of invasive leaders per tumor organoid in (A). For MMTV-Neu, n=116 organoids from 4 mice. For MMTV-PyMT, n=245 organoids from 10 mice. For C3(1)/Tag, n=104 organoids from 4 mice. Data are presented as mean±SD. *p<0.05 and **p<0.01. p value was determined by two-sided t test. (D) The percentage of invasive tumor organoids from the three mouse models in (A) as a function of time in culture (in hr). Onset of invasion was defined as the first instance of protrusive cell motility into collagen I matrix.
Figure 10:
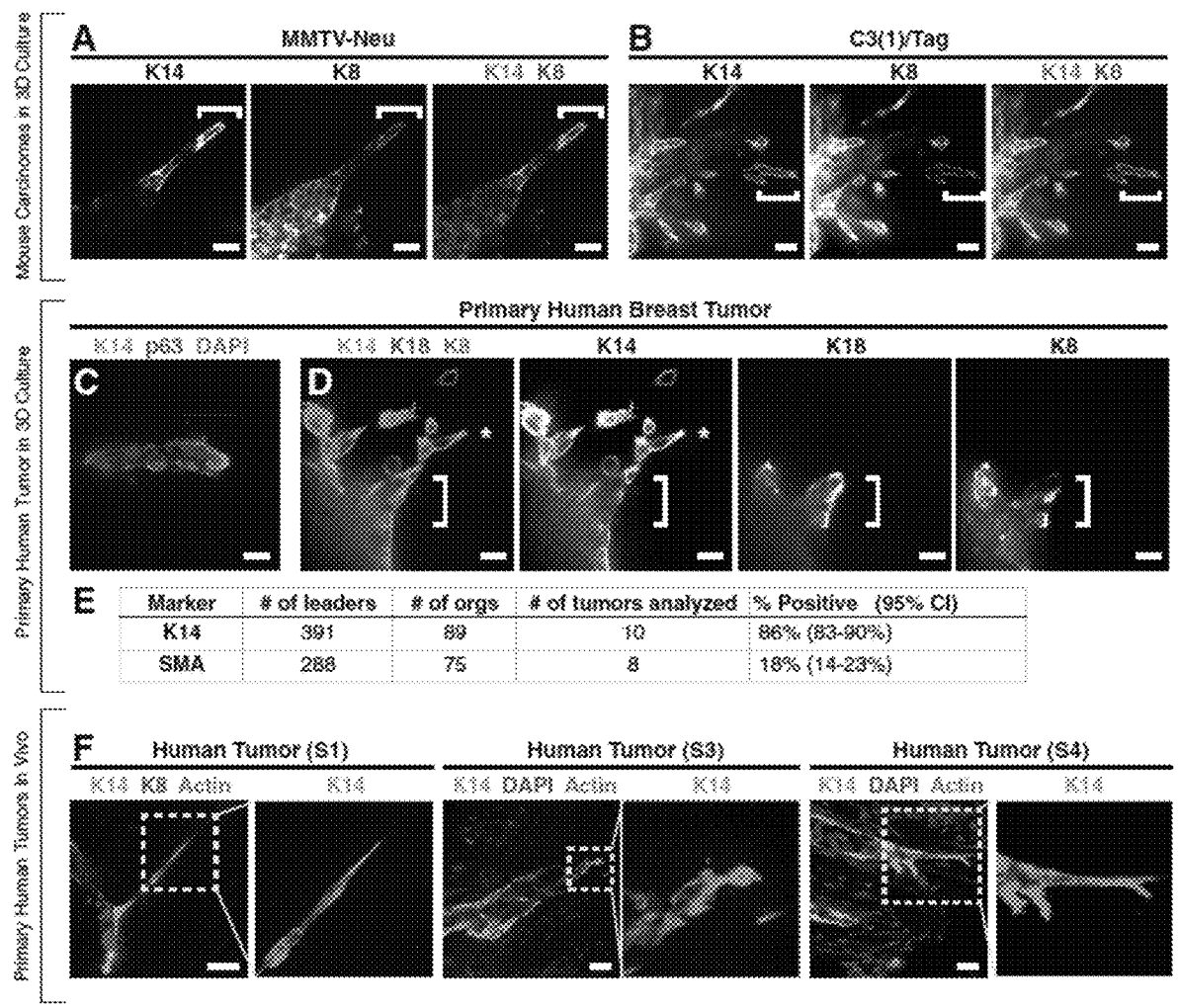

FIG. 10. K14+ Invasion in Primary Mouse Mammary Carcinomas and Human Breast Tumors, Related to FIG. 3 (A) Micrograph of a leader cell from a MMTV-Neu tumor organoid stained with K14 and K8. (B) Micrograph of leader cells from a C3(1)/Tag tumor organoid stained with K14 and K8. (C and D) Micrographs of leader cells in primary human breast tumor organoids stained with K14, p63 and DAPI (C), or K14, K18, and K8 (D). In (D), star, a K14+ leader cell; vertical bracket, K14+K8+K18+ cells just proximal to the leader cell. (E) Frequency of leader cells expressing K14 or SMA in human breast tumor organoids. 95% confidence intervals for each proportion denoted in parentheses. (F) Micrographs of K14+ cells in vivo from primary human samples (8, 10, and 11). Insets demonstrate collective strands of individually protrusive K14+ cells. The scale bar represents 20 mm in (A-D, and F: middle and right panels) and 100 mm in (F: left panel).

Figure 11:
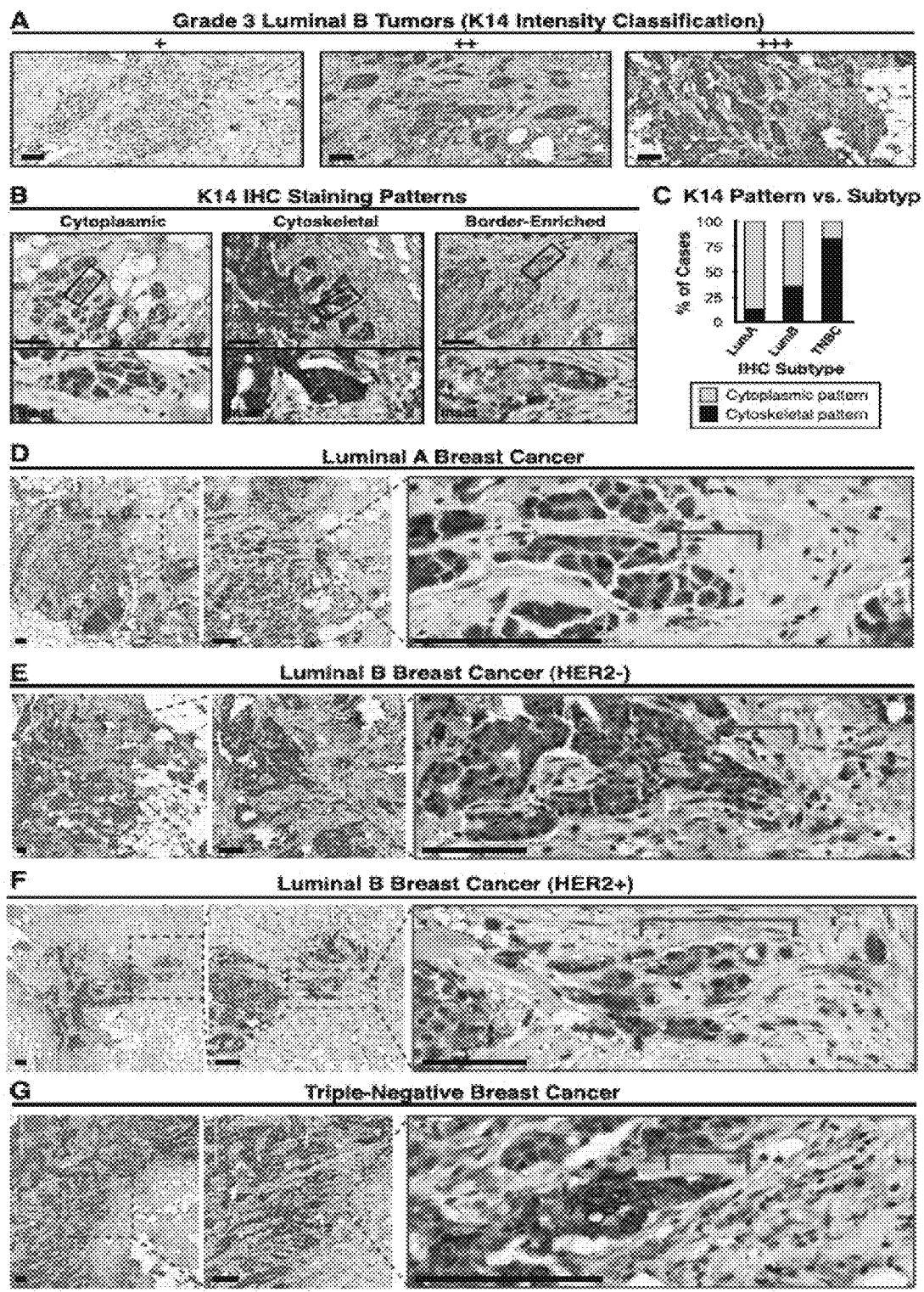

FIG. 11. K14 Is Expressed in Primary Human Breast Cancers In Vivo, Related to FIG. 3 (A) Representative micrographs of low (+), medium (++), or high (++) K14 staining intensity among grade 3 lumenal B human breast tumors. (B) Representative micrographs of the distinct K14 immunohistochemical staining patterns observed in primary human breast specimens. Insets, collective invasion fronts. (C) The frequency of cases with cytoskeletal or cytoplasmic only K14 staining patterns stratified by IHC-defined breast cancer subtype. (D-G) Representative micrographs of K14+ collective invasion fronts from archival specimens representing the major subtypes of breast cancer. Red bar, leader cells. Scale bars in (A-B, D-G) represent 100 mm.

Figure 12:
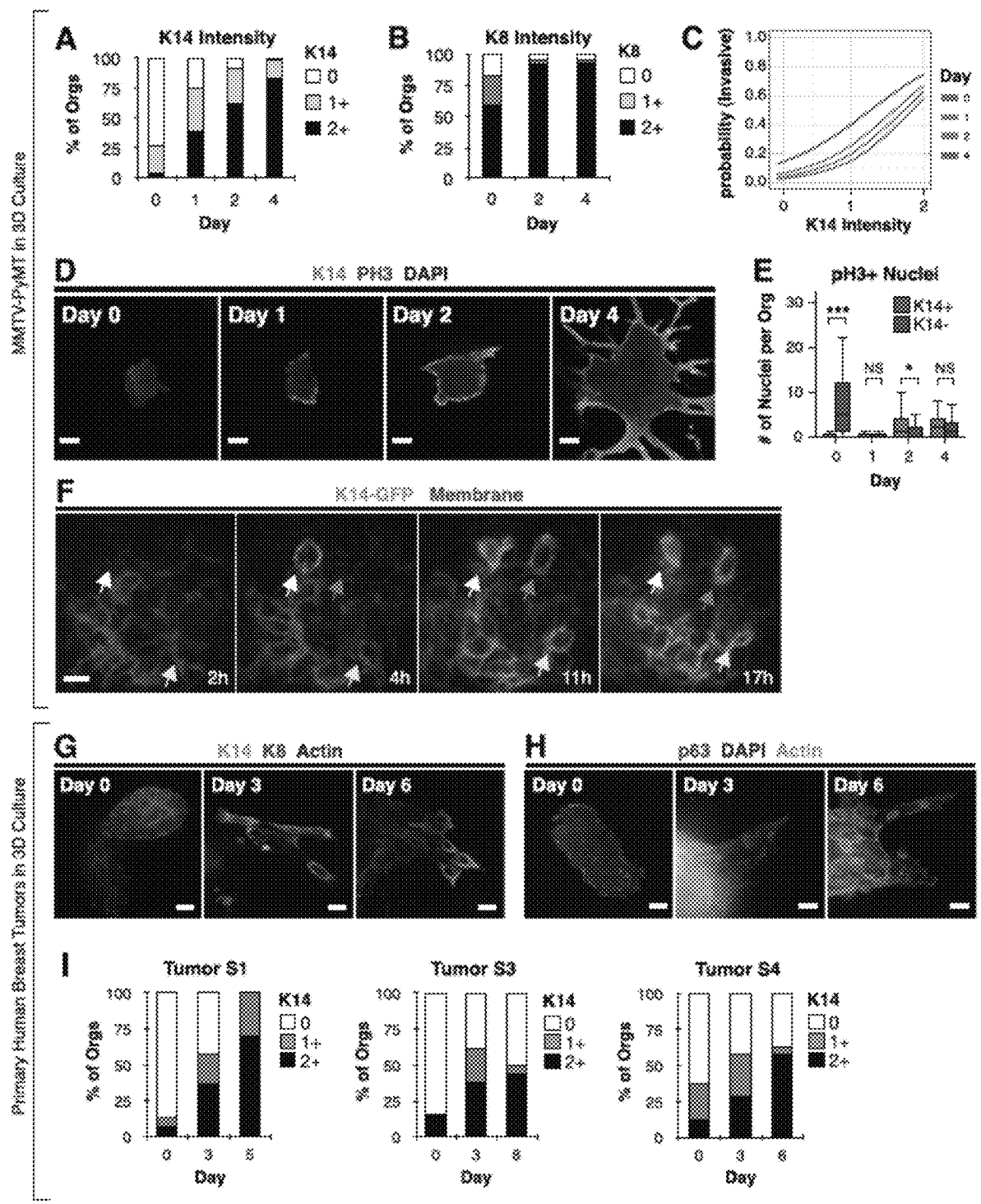

FIG. 12. K14+ Leaders Originate from Lumenal Tumor Cells, Related to FIG. 4 (A) K14 intensity was quantified into 0 (no or few), 1 (intermediate), 2 (bright) K14 signal. N=920 orgs, from 5 to 8 mice per day. (B) K8 intensity was quantified into 0 (no or few), 1 (intermediate), 2 (bright) K8 signal. N=269 orgs, from 3 mice per day. (C) Predicted probability function of invasion as a function of K14 intensity and day in culture. Logistic regression was conducted fitting the dependent variable invasion to the product of independent variables [K14 intensity]×[day in culture]. K14 intensity and day in culture contribute to the model with p<0.05. (D) Micrographs of mammary tumor organoids grown in 3D collagen matrix, stained with K14, pH3, and DAPI. (E) The number of mitoses (pH3+) per tumor organoid (Org) as a function of time. Data presented as boxplots. nR31 orgs per time-point. ***p<0.0001. *p<0.05. p value determined by two-sided t test. N=137 orgs in total, from 2 mice per condition. (F) Time-lapse microscopy of tumor organoids derived from MMTV-PyMT; K14-GFP mice at day 0 postplating (en face view). Colored arrowheads, lumenal tumor cells initially GFP− which become GFP+. See Movie 11 (not shown). (G) Micrographs of human tumor organoids (sample 11) grown in 3D collagen matrix, stained with K14, K8 and phalloidin. (H) Micrographs of human tumor organoids (sample 8) grown in 3D collagen matrix, stained with p63, DAPI and phalloidin. (I) Bar graphs of K14 intensity in human tumor organoids versus day in culture for human tumor organoids (for samples 8, 10, 11). n=44-78 orgs per human tumor. K14 intensity was quantified into 0 (no or few), 1 (intermediate), 2 (bright) K14 signal. Scale bars are 40 mm in (D), 20 mm in (G-H), and 10 mm in (F).

Figure 13:
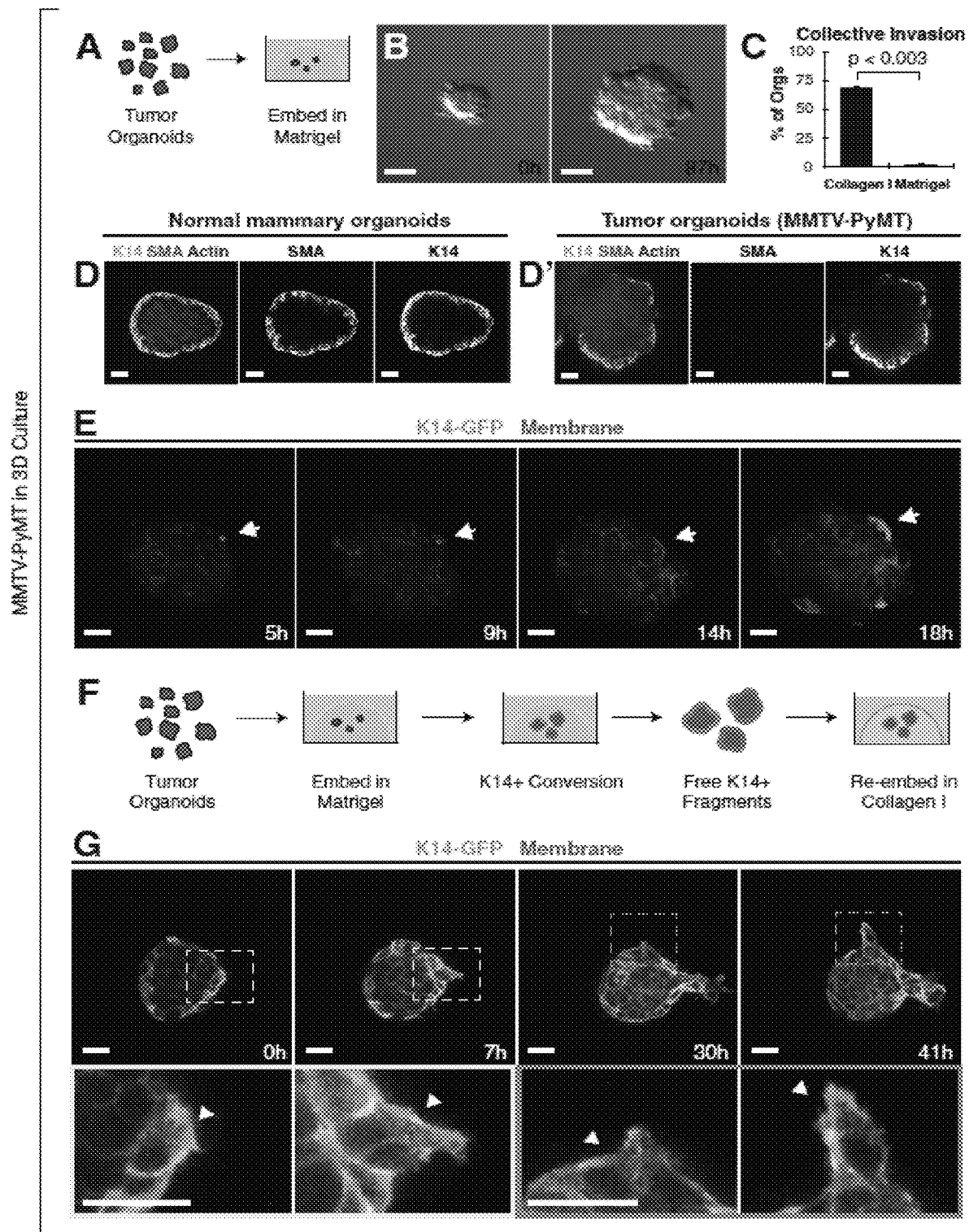

FIG. 13. K14+ Cells Acquire Leader Cell Behaviors Specifically in Collagen-I-Rich Local Microenvironments, Related to FIG. 5 (A) Schema of the 3D Matrigel organoid assay. Tumor organoids are embedded in 3D Matrigel. (B) Time-lapse DIC microscopy of an embedded MMTV-PyMT mouse mammary tumor organoid. The tumor organoid does not initiate protrusive collective invasion into Matrigel. (C) Invasion was quantified by scoring protrusive morphology of cancer cells in contact with the ECM. Data presented as mean±sd. N=431 organoids, 3-4 mice. p value determined by two-sided t test. (D and D0) Micrographs of normal mammary organoids and mammary tumor organoids cultured in Matrigel and stained with K14, SMA and phalloidin. (E) Time-lapse sequence of K14-GFP; MMTV-PyMT tumor organoid embedded in 3D Matrigel. Arrows, single GFP negative cell that becomes GFP positive. See Movie 12 (not shown). (F) Schematic of matrix switching experiment. MMTV-PyMT mammary tumor was digested into tumor organoids and embedded in 3D Matrigel. Following K14+ conversion, tumor organoids were freed and re-embedded in 3D collagen I. (G) Time-lapse microscopy of MMTV-PyMT; K14-GFP tumor organoid preconditioned in Matrigel and then re-embedded in collagen I. Arrowheads, K14-GFP+ cells that switch to protrusive morphology and lead collectively invading strands of cells. See Movie 13 (not shown). Scale bars represent 50 mm in (B) and 20 mm in (D, E, G).

Figure 14:
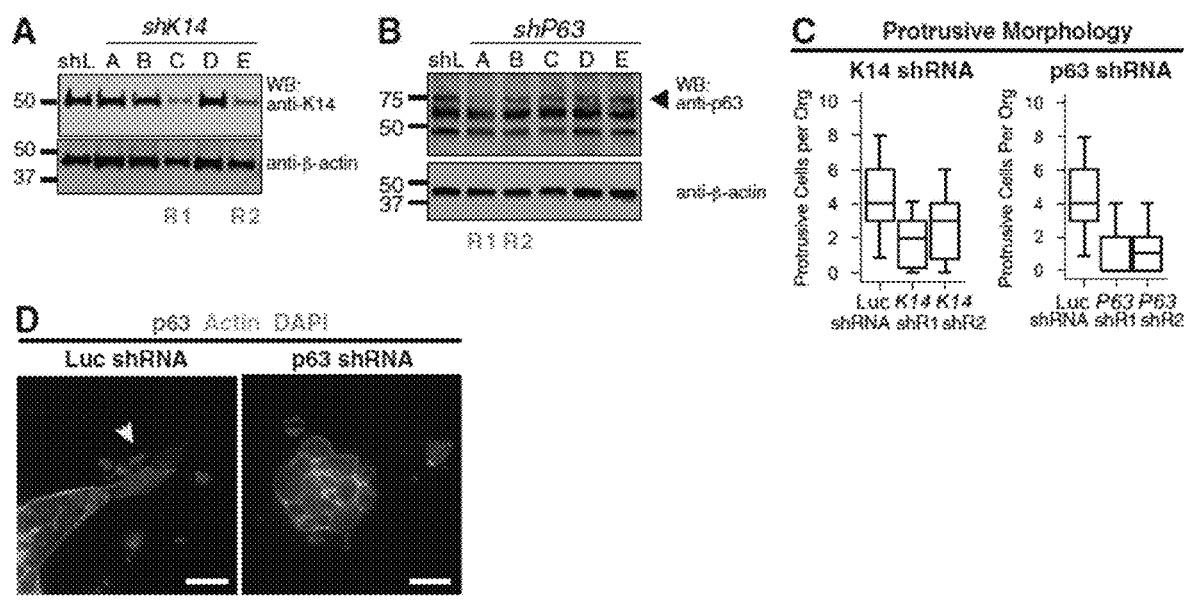

FIG. 14. Basal Epithelial Genes K14 and p63 Are Required for Collective Invasion in 3D Culture, Related to FIG. 6 (A) Western blotting for K14 expression was conducted on total cell lysates from MMTV-PyMT tumor organoids transduced with lentiviral particles encoding shRNAs against luciferase control (labeled shL) or one of five unique K14 constructs (labeled A-E). (B) Western blotting for p63 expression was conducted on total cell lysates from MMTV-PyMT tumor organoids transduced with lentiviral particles encoding shRNAs against luciferase control (labeled shL) or one of five unique p63 constructs (labeled A-E). (C) The number of protrusive cells in Luc shRNA, K14 shRNA, and p63 shRNA transduced organoids presented as boxplots. The number of protrusive cells was determined from fixed collagen I embedded organoids. N=54-122 organoids from 3 independent experiments. All comparisons against Luc shRNA yielded p values <$1\times10^a$-5. P values determined by two-sided t test. (D) Micrographs of MMTV-PyMT tumor organoids transduced with Luc shRNA and p63 shRNA stained with p63, DAPI, and phalloidin. Scale bar represents 20 mm in (D).

Figure 15:
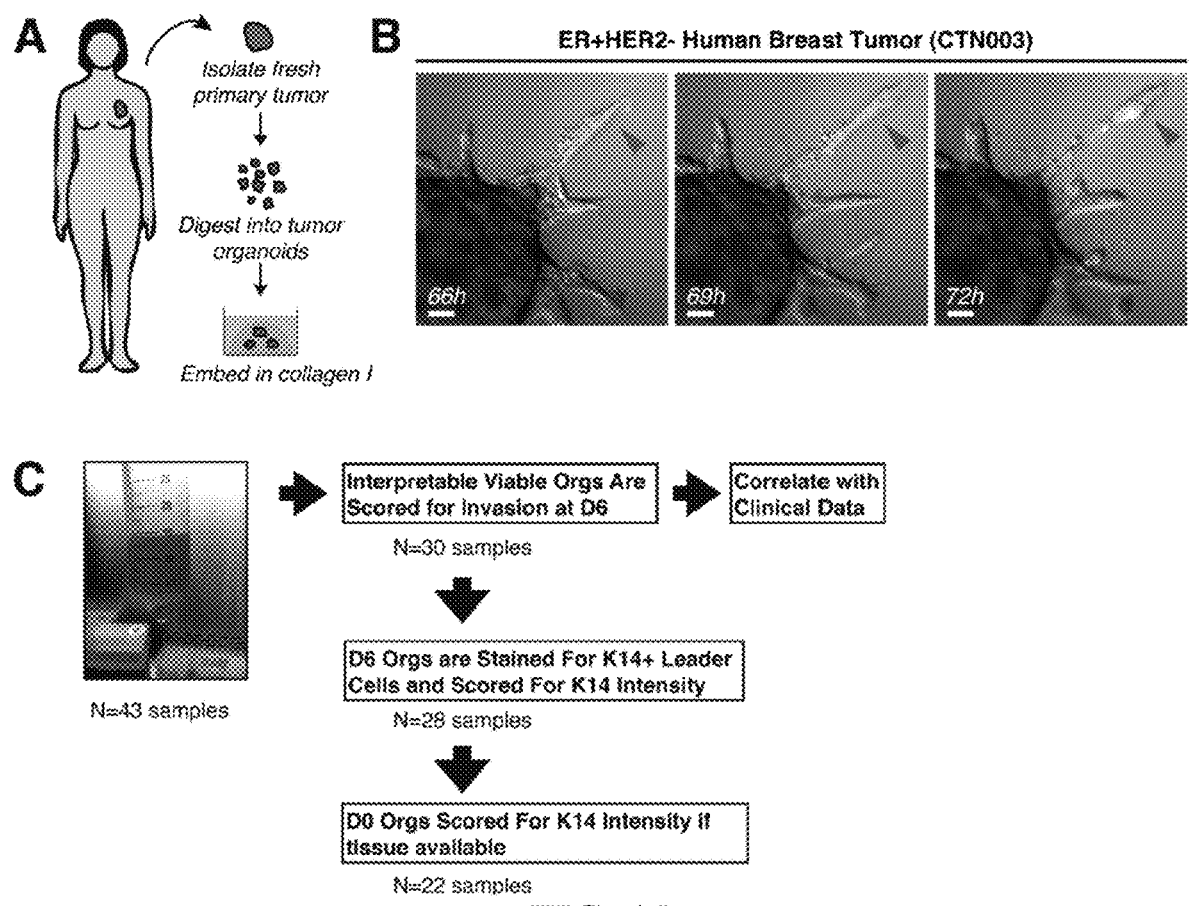

FIG. 15. (A) Primary human tumor organoids were isolated from fresh patient samples (N=43 patient samples). (B-C) Samples were processed for organoids, assayed for invasion, K14+ leader cells, K14 intensity and K14 conversion.

Figure 16:
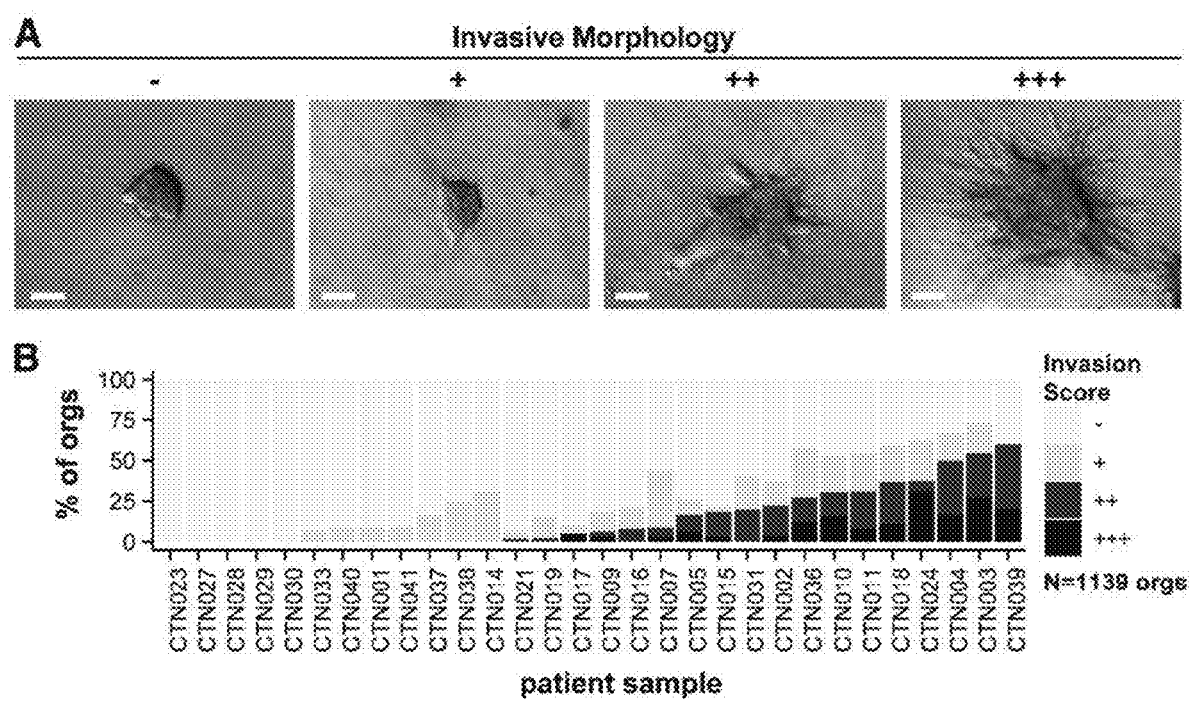

FIG. 16. (A) Primary human tumor organoids were scored for invasive morphology into four categories. (B) Invasive morphology was scored on viable patient samples (N=30 patient samples; N=1139 organoids) and sorted from the least to most invasion.

Figure 17:
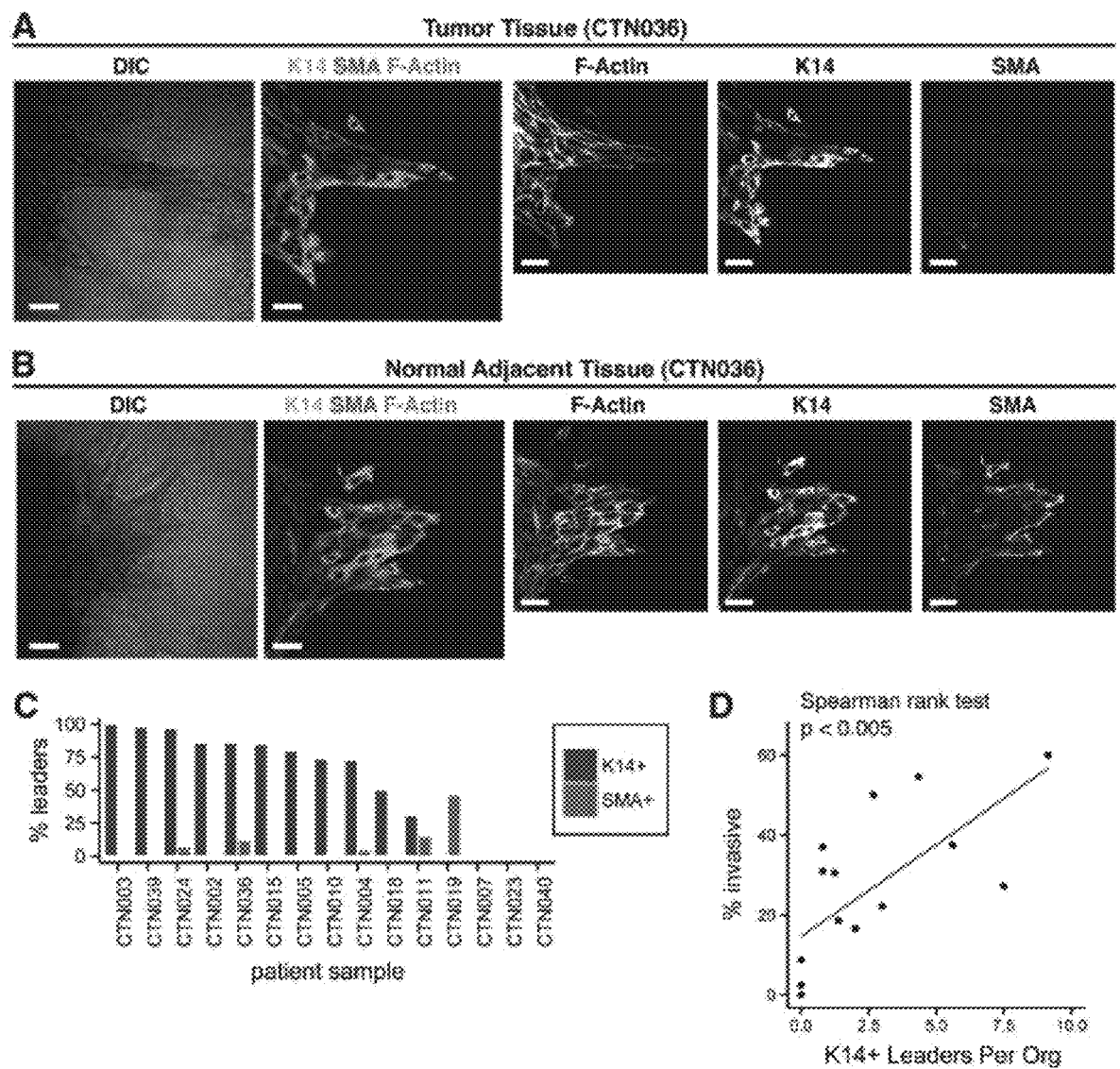

FIG. 17. (A-B) Leader cells were stained for keratin-14 (K14), smooth muscle actin (SMA), and phalloidin (F-actin) in human organoids from primary tumor (A) or normal adjacent tissue (B). (C) Leader cells were scored for positivity for K14 and SMA. (D) The number of K14+ leader cells per organoid was plotted versus the % of invasion (defined as ++ or +++). P-value was determined by spearman rank test.

Figure 18:
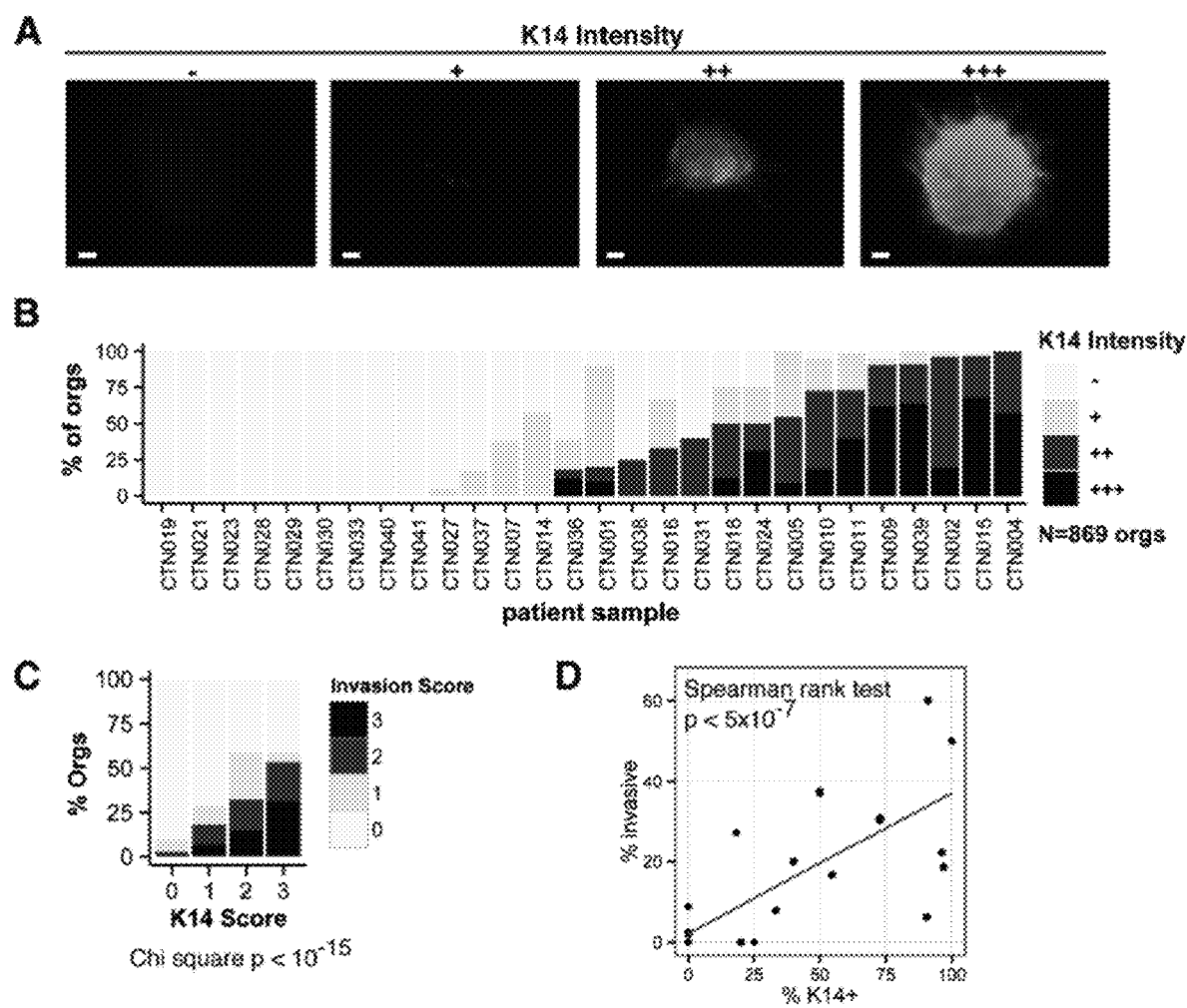

FIG. 18. A) Primary human tumor organoids were scored for K14 intensity into four categories. (B) K14 intensity was scored on viable stained patient samples (N=28 patient samples; N=869 organoids) and sorted from the least to most K14 intensity. (C) On a per organoid basis, K14 intensity strongly correlated with invasion. P-value determined by chi-square test. (D) The % of K14+ samples (defined as ++ or +++) was plotted versus the % of invasion (defined as ++ or +++). P-value was determined by spearman rank test.

Figure 19:
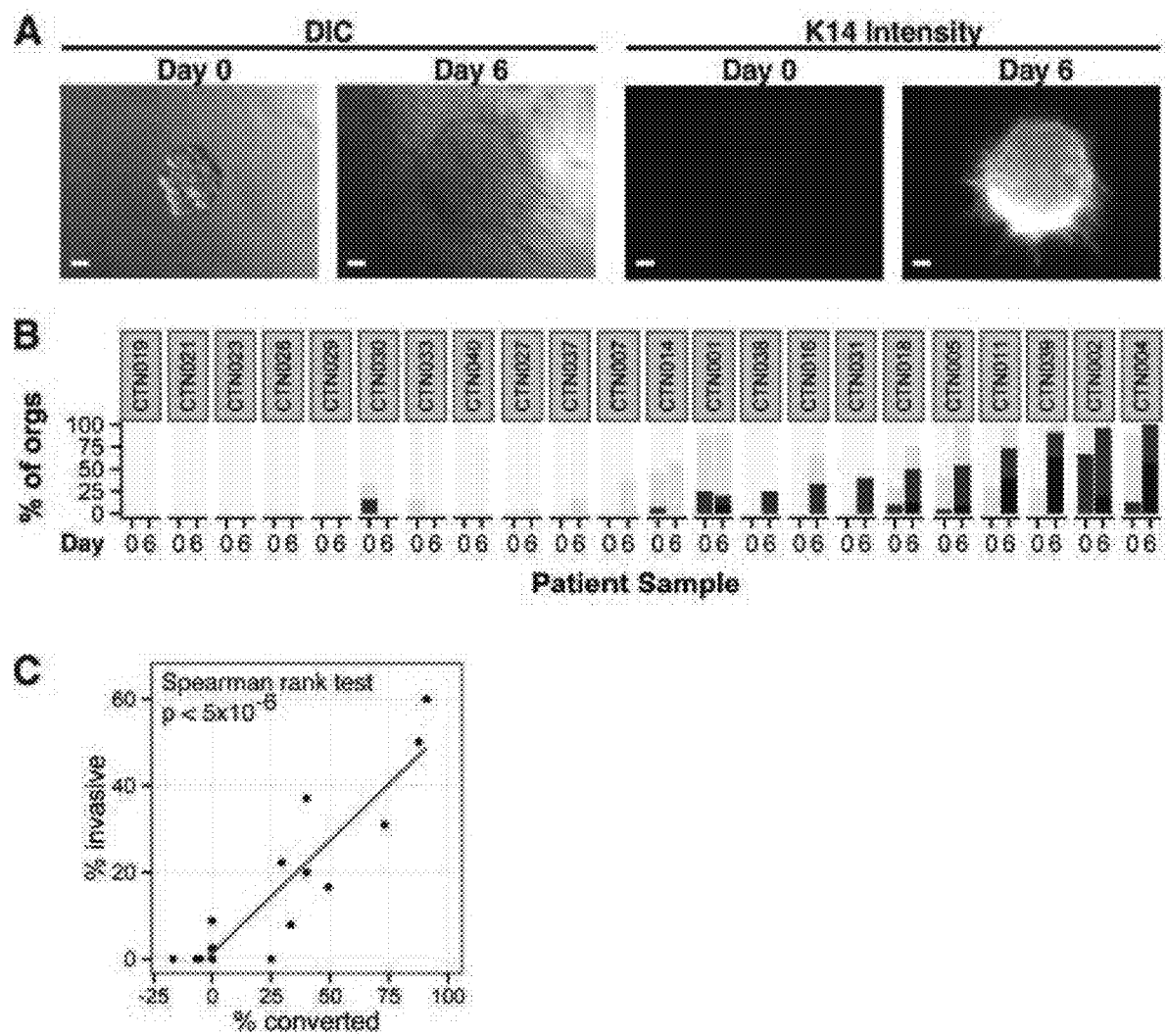

FIG. 19. A) Primary human tumor organoids were scored for K14 intensity also at Day 0 and compared with Day 6 when tissue was available. (B) K14 conversion was scored on viable stained patient samples (N=22) and sorted from the least to most K14 conversion. (C) The % of K14+ conversion (defined as the change in % from Day 0 to Day 6) was plotted versus the % of invasion (defined as ++ or +++). P-value was determined by spearman rank test.

Figure 20:
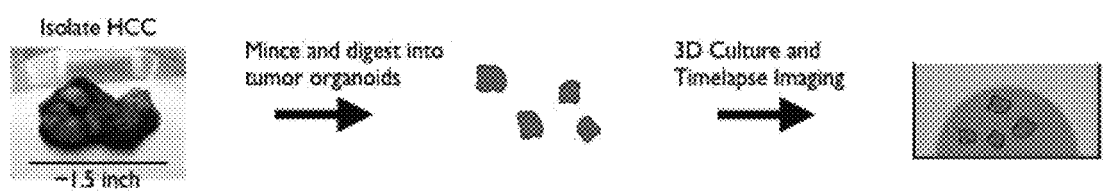

FIG. 20. Hepatocellular carcinomas were isolated from murine livers, chopped with a scalpel, digested with enzymes, and centrifuged to separate single stromal cells away from epithelial tumor organoids. Organoids were then explanted into collagen I gels.

Figure 21:
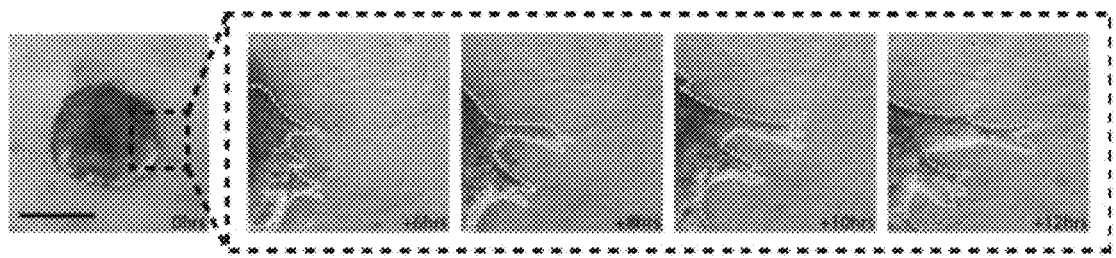

FIG. 21. Hepatocellular carcinoma organoids consisting of several hundred cells were cultured in collagen I gels. A few (5-15) strands of cancer cells per organoid invaded into the surrounding collagen I. As with breast tumor organoids, the invasive leader cells were individually protrusive and strongly interacted with the collagen I. The leader cells can be molecularly profiled in situ by various techniques, including but not limited to immunohistochemistry, immunofluorescence, and RNA based detection methods. Alternately, the leader cells can be isolated away from the bulk cancer cells, for example by fluorescence activated cell sorting or laser capture microdissection and then profiled for DNA, RNA, protein, or protein activity/modifications.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Invasion is a fundamental step in tumor progression and a driving force for metastasis. Although invasion is commonly conceptualized as a single-cell process, the majority of solid tumors display features of collective invasion in which cells invade cohesively as a multicellular unit (Friedl et al., 2012; Leighton et al., 1960). A central problem in collective invasion is how a group of adherent epithelial cancer cells acquires motile invasive behavior (Friedl and Gilmour, 2009; Gray et al., 2010; Polyak and Weinberg, 2009).

One solution is for cancer cells to rely upon the motility of migratory stromal cells, such as fibroblasts (Gaggioli et al., 2007) or macrophages (Condeelis and Pollard, 2006; DeNardo et al., 2009). However, mammary tumors also contain multiple subpopulations of tumor cells with distinct genotypic and phenotypic characteristics. Importantly, this cellular heterogeneity is associated with differences in metastatic potential and therapeutic response (Almendro et al., 2013; Fidler, 2003). It remains unclear how these subpopulations of cancer cells contribute to collective invasion.

Clinically, the transition from in situ to invasive breast cancer correlates with a strong reduction in overall survival, but the molecular basis of this transition has remained elusive (Polyak, 2010). The challenge of transitioning to a motile phenotype is particularly acute in mammary lumenal epithelial cells, as these cells are normally connected by extensive intercellular junctions and display less spontaneous motility than myoepithelial cells in real-time analyses (Ewald et al., 2008). Consistent with this concept, lumenal breast cancers have a more favorable average prognosis, but 10%-20% of cases eventually metastasize to liver, lung, or brain (Kennecke et al., 2010). Furthermore, luminal breast cancer cell lines are weakly invasive in 2D culture compared to basal subtypes (Neve et al., 2006).

We hypothesize that breast tumors accomplish collective invasion through cell-cell interactions among functionally distinct epithelial cancer cells within the primary tumor. To test this hypothesis, we developed 3D organoid assays to identify the most invasive cancer cells within a primary tumor in an unbiased fashion. In the present study, we applied these assays to demonstrate that the cells leading collective invasion are molecularly and behaviorally distinct from the bulk tumor cells and display a conserved, basal epithelial gene expression program.

The classic view of epithelial cancers was based on the assumption that phenotypically and genetically similar cancer cells were responsible for the majority of the important cellular and molecular attributes of a cancer cell. This is most strongly represented in the case of chronic myeloid leukemia in which a single molecular event (chromosomal translocation) creates an abnormal fusion protein that is diagnostic for the disease and required for its function. Most epithelial cancers instead exhibit considerable cellular and molecular heterogeneity among the cancer cells. This "tumor heterogeneity" is increasingly appreciated, but relatively few groups have proposed strategies to determine which of these various cancer genotypes and phenotypes are most important to disease progression.

The present inventors hypothesized that 3D culture models could be used to prospectively identify the most invasive cancer cells based on their behavior and functional attributes. We then used molecular techniques to describe these cells. The present inventors have also simplified the assay to capture the type of invasive behavior described herein. For example, in one embodiment, a thin pattern of collagen I can be laid on a glass coverslip and cells plated on top. Thus, in certain embodiments, the organoids/tissue/cells are cultured in an extracellular matrix gel. In certain embodiments, the extracellular matrix gel is a three-dimensional extracellular matrix gel.

The critical difference from past efforts is that the functional ability of the cancer cells to invade is the primary focus of the present assay; the molecular phenotype is the description of the cells that share this functional attribute. Previous approaches have almost all used one assay or another to purify a population with a specific molecular phenotype and then compare it to unsorted or alternately sorted populations. The limitation of that approach is that one needs to select the molecules in advance and a lot of time may be spent describing cellular populations that are more proliferative/invasive, etc. than the bulk average but nonetheless are not the cells that really dictate proliferation and invasion in vivo. Extensive experimental work by the present inventors has validated that the approach works and that the most invasive cells in 3D culture are also the most invasive in vivo and that they are strongly overrepresented in metastases.

The invasion assays of the present invention can also be used in the laboratory setting as an experimental tool. BD and others sell Matrigel-Invasion Kits, which have questionable physiologic relevance to in vivo invasion. The present invention represents a clear conceptual advance over other more primitive invasion assays, like the matrigel-invasion kits. More importantly, the present invention has been actually validated in vivo, such that we identify morphologically similar invasion at the invasive border and in specific matrix micro-environments. The assays of the present invention could replace Matrigel-Invasion as the new gold-standard for assaying invasion.

Accordingly, in one aspect, the present invention provides assays for identifying the invasive subpopulation(s) of a tumor. Researchers have been explanting cells and tissues into 2D and 3D ECM gels for decades. However, the present inventors are the first to couple this technology with the idea that these assays can be used to identify the most invasive cells in a tumor by their functional behavior. In one embodiment, the present invention can be used to identify invasive subpopulations in additional epithelial cancers (e.g., what is the most invasive cell type in a lung cancer). In another embodiment, the present invention may comprise personalized medicine assay based on a patient's own live tumor tissue to determine the identity and abundance of invasive subpopulations in their primary tumor. In yet another embodiment, the present invention may comprise a personalized medicine assay to determine the chemosensitivity of a patient's own metastases. We have shown that invasive leaders can be rare in the primary tumor but are typical of the metastatic site. Accordingly, the chemosensitivity of these cells to different therapies could be tested and the response of the patient's metastases can be predicted. This is distinct from past chemosensitivity proposals as it focuses on identifying a specific cancer cell subpopulation.

In further embodiments, the present invention can be used to quantify the fraction of cells in the tumor that can convert to K14+ when explanted into the assay. In other embodiments, the convertibility assay could be used for any molecular signature of invasive behavior. More specifically, the assay captures the fraction of cells in a tumor capable of initiating metastatic spread. The wide variation in inducibility of primary human breast tumors is captured in FIG. 19b. The tumors towards the right can very easily transition to the metastasis competent K14+ phenotype. Inducibility is expected to correlate with the likelihood that that specific patient will experience distant recurrences in the future. Convertibility can be assayed very robustly in very simple assays (e.g. thin layer of ECM in a multiwell plate).

In another aspect, the present invention contemplates that the molecular signature described herein (K14+, p63+, etc.) is characteristic of all highly invasive epithelial cancer cells. In one embodiment, the signature comprises keratin 14+, p63+, P-cadherin+, smooth muscle actin–. In other embodiments, each one of keratin 14+, p63+, P-cadherin+, and smooth muscle actin– can serve as a molecular marker. In a specific embodiment, K14+ is the biomarker, and so on. Accordingly, this subpopulation represents a target for cancer therapy.

In another aspect, the abundance and/or locations of invasive leader cells correlates with patient progress. The molecular signature described herein can be used as a biomarker to assess individualized risk of recurrence/distant metastasis.

In yet another aspect, the present invention provides agents for modulating targets involved in the basal invasive molecular program. We have identified not only the cell type, but also specific molecular targets. Specifically, we define the cell population (basal leaders) as important for invasion, but also define specific molecular targets whose inhibition may have therapeutic benefits in blocking invasion and metastasis. We have identified multiple molecular targets that when inhibited result in either a block of the invasive program (e.g. p90RSK or p63) or a block of the invasive behavior of invasive leader cells (e.g. K14, FAK, Src). We have shown that shRNA inhibition of K14 blocks invasion in vitro and in vivo. We have identified small molecule inhibitors of multiple of these targets (e.g. FAK inhibitor (Pfizer).

In particular embodiments, the present invention provides assays that enables prospective identification of the most invasive cancer cells within a tumor and their subsequent molecular characterization. The present invention can be used to detect the molecular signature of a specific population of invasive cells first identified from our studies, which we call basal leader cells.

In certain embodiments, live tissue from a patient's own tumor can be harvested and cultured in this assay to reveal the most invasive cells in that patient's tumor. In mouse models, the most invasive population in the live cell assay predicted the cellular identity of micrometastases at distant sites in the body. In addition, the frequency of invasion in the live cell assay between mouse models appears to correlate with the published rate of metastatic spread to the lungs. The live cell assay therefore provides an ability to estimate the likelihood of distant metastases as well as to predict the molecular characteristics of those cells. The cellular identity of the most invasive population could be used to estimate risk of recurrence or to personalize the course of treatment for the patient. If the cellular identity corresponds to basal leader cells, we predict an increased risk of recurrence and resistance to chemotherapy.

We have defined a specific molecular signature, the basal leader signature, (keratin 14+, p63+, P-cadherin+, smooth muscle actin–) that correlates with the most invasive subpopulation in mouse tumor models and with the cellular identity of micrometastases. This gene expression signature could be used to identify invasive subpopulations in sections from fixed tissue from archival human tumors. Alternatively, the presence of this gene signature could be determined by mRNA expression analysis from archival sections to generate a composite score. If validated in large cohorts this gene signature could be developed into a diagnostic assay based on the composition and abundance of different highly invasive subpopulations within the tumor. This gene expression information could then be used to estimate the risk of local recurrence or distant metastases. The signature can also comprise individually each of the markers listed above, e.g., K14+.

A major barrier to the development of therapies to limit the invasive and motile properties of cancer cells is our very incomplete understanding of the cell and tissue basis of cancer invasion in vivo. The critical events of invasion, dissemination, systemic spread, and establishment of distant metastases occur episodically, deep within the body over a period of months to years. Recent work from multiple labs, including our own, has led to the in vivo observation of cell dynamics in intact mammary tumors. A surprising result of these studies was that most cancer cells in established epithelial tumors were non-motile. Histological examination of breast tumors has revealed striking cellular and molecular heterogeneity, but analysis of fixed sections cannot distinguish the relative contributions of these subpopulations to invasion. To solve this problem, we developed a suite of isolation, culture, gene manipulation, and imaging techniques to enable the real-time analysis of invasion and dissemination in primary tumors within 3D tumor microenvironments. We developed protocols for culturing normal epithelium and mammary tumors from primary mouse and human sources. We explant primary epithelial fragments (500-1000 cells each) into 3D extracellular matrix (ECM) gels (FIG. 1A) and have shown that the patterns of growth in 3D culture closely model the in vivo organization (e.g. FIG. 1B vs. 2A).

We explanted metastatic mammary carcinomas (MMTV-PyMT) into Matrigel and observed confined growth without dissemination in Matrigel and vigorous sustained dissemination into collagen I. It was known that smooth muscle actin (SMA) positive myoepithelial cells are lost early in this model, paralleling human luminal B breast cancer. We next conducted a systematic RNA expression analysis of normal and tumor tissue growing in both matrices and observed that the contractile smooth muscle program was lost, but that the majority of other myoepithelial specific genes (e.g. keratin-14 (K14)) displayed only modest reductions. Our imaging studies revealed that the most common leaders cells during invasion in 3D culture are epithelial cells that express basal markers (K14+), but lack the mature smooth muscle program (SMA–, FIG. 1B, left panel). The keratin-14+ cells were generally also positive for p63+ and P-cadherin. In real-time analyses in 3D culture these cells actively sort to the basal surface of tumor fragments. These cells are a minor fraction of total epithelial cells, but led invasion in 916 of 1001 invasive strands in 3D culture (FIG. 1B). By time-lapse confocal microscopy these cells are highly protrusive into matrix, and can disseminate and survive as single cells for over 48 hours (FIG. 1C-D). Using both antibodies and a real-time keratin-14 fluorescent biosensor, we revealed that a basally positioned keratin-14+ exists in vivo, even in poorly differentiated carcinomas. By 3D reconstruction of tumor tissue in vivo, we find that although overall K14+ SMA− cells account for less than 10% of tumor, these cells are enriched at the tumor-stroma border and in lung metastases (FIG. 2A,C). We have identified these same basal cells in each of three additional mammary carcinoma models we have examined (FIG. 2B), suggesting that these cells may generally lead the invasive and metastatic properties of many or most breast tumor subtypes. When we challenged with doxorubicin, the K14+ cells were strongly overrepresented in the intrinsically resistant cells. Our hypothesis is that the invasion, dissemination, and metastasis of this luminal breast cancer is driven by a basal K14+; P63+; SMA− subpopulation with intrinsic chemoresistance.

Mature myoepithelial cells function as tumor suppressors, but aggressive basal subtype cancers express a subset of myoepithelial markers. Recent studies have focused on the role of stromal cells in leading breast tumor invasion. We previously revealed that normal myoepithelial cells have higher intrinsic motility than luminal cells and our current data suggest that mammary tumors co-opt this motility program. Our working hypothesis is that basal epithelial subpopulations can lead the invasion and metastasis of breast tumors, including in luminal subtypes. Our data identify biological heterogeneity within the epithelial cells of the tumor as a potential driving force for metastasis and suggest even a small basal subpopulation can have a large effect on the dynamics of a luminal breast tumor. Our work could have particular importance for patients with metastatic breast cancer, as long-term control of tumor invasion and metastasis will likely require suppression of each potential leader population.

In one embodiment, tumors are surgically isolated and then minced with a sterile scalpel. Tumors are enzymatically digested in a mixture of collagenase and trypsin to yield small "organoids" that contain 500-1000 tumor cells. These organoids are then explanted into 3D gels of extracellular matrix proteins, most typically collagen I gels. Over time in culture invasive strands emerge from the organoids and the invasive leaders can be molecularly profiled in situ or following laser capture or other microdissection techniques.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Experimental Procedures

Mouse Lines and Breeding.

Mice used in this study were backcrossed onto and maintained on the FVB/n background in a specific pathogen-free facility Animal protocols were approved by the Johns Hopkins IACUC. FVB/N-Tg(MMTV-PyVT)634Mul/J (MMTV-PyMT) (Guy et al., 1992a), FVB/N-Tg(MMT-Vneu)202Mul/J (MMTV-Neu) (Guy et al., 1992b), FVB-Tg (C3-1-TAg)cJeg/JegJ (C3(1)/Tag) (Maroulakou et al., 1994), and B6.129(Cg)-Gt(ROSA)26Sortm4(ACTBtdTomato,−EGFP)Luo/J (mT/mG) (Muzumdar et al., 2007) mice were obtained from the Jackson Lab. K14-GFP− actin mice (Vaezi et al., 2002) were a generous gift from Elaine Fuchs (Rockefeller University). For confocal timelapse experiments, MMTV-PyMT mice were crossed with mT/mG mice and/or K14-GFP− actin mice.

Analyses of Fresh Primary Human Tumors.

Primary breast cancers were acquired in accordance with IRB exempt protocols NA_00052607 and NA_00077976 (Nguyen-Ngoc et al., 2012). In brief, each tumor sample was deidentified prior to receipt with limited prespecified clinical information provided with each sample. The tumor sample was kept in cold Dulbecco's modified Eagle's medium (DMEM) when in transit. The tumor sample was rinsed with antibiotic wash, minced, and then digested in collagenase with or without trypsin. Tumor organoids were treated with DNase and separated out by differential centrifugation at 1,500 rpm 3 4-6 spins. Tumor organoids were then allocated to either Matrigel or 3D collagen I and cultured in human mammary epithelium medium containing insulin, EGF, hydrocortisone, and cholera toxin. Medium was replaced every 3 to 4 days.

Statistics.

Statistical analysis was conducted using R. For all box-plots, the whiskers represent the 5th and 95th percentiles. All tests used and p values are specified in the FIG. legends. $p<0.05$ was considered significant. Additional materials and methods, including isolation of tumor organoids, antibodies, and staining procedures used, are described in the Extended Experimental Procedures.

Extended Experimental Procedures

Antibodies and Immunofluorescence.

For immunofluorescence of tumor organoids cultured in 3D gels, gels were fixed in 4% paraformaldehyde, permeabilized with Triton-X/lx PBS, and blocked in 1×PBS+10% fetal bovine serum and 1% BSA. Primary antibodies were incubated ~8 hr at room temperature or overnight at 4 C at the dilutions listed below in antibody diluent, 1×PBS+1% fetal bovine serum and 1% BSA. Secondary antibodies coupled to Alexa Fluor 488, 562, or 647 (Invitrogen) were incubated ~4 hr at room temperature. Where indicated, phalloidin was added at 1:100 dilution to stain F-actin positive cell membranes.

For immunofluorescence experiments of thick tumor tissues (100 mmor greater), tissue organoids were fixed overnight in 4% paraformaldehyde, embedded in OCT, and cut into sections on a cryostat. In this case, primary antibody incubation was performed in antibody diluent, for 2 to 3 days at 4 C, followed by secondary antibody incubation for 1 to 2 days also at 4 C. Overlapping z-stacks were captured using a high speed confocal spinning disc microscope, and the z-stacks were assembled using Fiji software, and custom scripts. To estimate the relative distance of cell populations from the tumor-stromal border, pixels were classified as K14+, K14− (mTomato+K14−), or stroma (F-actin+mTomato−). For each K14+ or K14-pixel we then identified the nearest neighboring stromal pixel. Using Fiji software, we calculated the Euclidian distance map. Then using R software, we tabulated the total number of pixels at any given distance from stroma. All custom scripts available upon request.

Primary antibodies were Cytokeratin 14 (Covance, PRB-155P), Cytokeratin 5 (Covance, PRB-160P), p63 (Epitomics, 5353-1, or Santa-Cruz, sc-8431), SMA (Sigma, A5228), K8 (TROMA-1c) (Developmental Studies Hybridoma Bank, 386-113626), K18 (Epitomics, 1924-1), P-cadherin (Life Technologies, Clone PCD-1 or Novus, NBP1-59222), Myhll (Santa-Cruz, sc-6956), E-cadherin (Invitrogen, 13-1900), Phospho-histone H3 (Ser10) (Cell Signaling Technologies, #9701), and Calponin (Millipore, 04-589).

Immunohistochemistry of Primary Human Tumor Sections.

K14 protein expression was evaluated in formalin-fixed paraffin-embedded primary tumors by immunohistochemistry in accordance with IRB protocol NA_00003308. Five-mm sections were treated with DAKO target retrieval solution for 20 min according to the manufacturer's recommendations and then incubated for 1 hr with an anti-human-K14 rabbit polyclonal antibody (Covance PRB-155P) at a concentration of 2.5 mg/ml, using an automated slide stainer (DAKO). Secondary reagents (LSAB2 secondary reagent system) were supplied by DAKO and used according to the manufacturer's specifications.

The intensity of staining in the cancer cells was scored as +(low to no staining), ++, or +++(intense staining). The pattern of staining was scored as primarily cytoplasmic or cytoskeletal with or without enrichment at the border of collective invasive units. Scoring was conducted in a blinded manner by a pathologist observer (EG). The breast cancer subtype was determined for each specimen according to St. Gallen Consensus Guidelines using surrogate IHC criteria, including estrogen receptor (ER), progesterone receptor (PR), HER2, and Ki-67 status (Goldhirsch et al., 2013). Lumenal A tumors were defined as those that were ER positive and Her2 negative and had PR>20% and Ki-67<20%. Lumenal B tumors were defined as those tumors that were ER positive and any of the following: PR % 20%, Ki-67 R 20%, or Her2 amplified. TNBC tumors were defined as those tumors that were negative for ER, PR, and Her2.

Isolation and 3D Culture of Murine Organoids.

We isolated organoids from primary mammary tumors and normal mammary gland using previously described techniques (Nguyen-Ngoc et al., 2012). MMTV-PyMT tumors were harvested from mice at 12-16 weeks of age, C3(1)-Tag tumors were harvest at 22-24 weeks of age, and MMTV-Neu tumors were harvested at 40-50 weeks of age, coinciding with palpable solid tumors. For each mouse, we surgically isolated the largest tumor and processed it as above. Briefly, we dissected tissue into epithelial organoids by a combination of mechanical and collagenase/trypsin digestion. We then separated these organoids from single cells by differential centrifugation. Any incompletely digested large tumor organoids were removed prior to differential centrifugation. We also added additional rounds of differential centrifugation as needed to remove single cells. The final pellet was composed of epithelial organoids, each containing 200-1000 cells.

We then embedded organoids in type I rat tail collagen gels (BD Biosciences 354236) or 3D Matrigel (BD Biosciences 354230). All cultures were set up in 24-well coverslip bottom plates (E&K Scientific EK-42892), or 2-well or 4-well coverslip bottom chambers (Nunc 155383). Acid solubilized rat tail collagen I gels (3 mg/ml collagen I, pH 7-7.5) were prepared as previously described (Nguyen-Ngoc et al., 2012). For each matrix, organoids were mixed to yield a suspension of 1-2 organoids/ml. A 100 ml suspension of organoids was plated in each well on the 37° C. heating block, followed by incubation at 37° C. to allow polymerization. All murine samples were cultured in 1 ml of 2.5 nM FGF2 in murine organoid media.

Image Acquisition and Quantification.

Confocal images were acquired using a custom spinning disc microscope using a 40× cAPO oil objective. For z-stacks, 2 mm spacing was used. Representative single z planes are presented unless noted. Images were recorded at 1,024×1,024 square pixels representing 0.17 mm per pixel. Second-harmonic generation microscopy was conducted using a Zeiss LSM 710 laser-scanning microscope at 63× water objective. Red-green-blue (RGB) images were assembled using Fiji software and custom scripts.

Time-Lapse Imaging.

Live differential interference contrast (DIC) imaging of tumor organoids was conducted using a Zeiss Cell Observer system with a Zeiss AxioObserver Z1 and a AxioCam MRM camera. In general, images were collected at 20 min intervals with exposure times of ~250 ms. Live confocal time-lapse imaging was performed using a custom spinning disc microscope (Ewald, 2013). Temperature was held at 37° C. and CO2 at 5%.

Flow Cytometry.

Primary tumors from MMTV-PyMT mice carrying a K14-GFP reporter were harvested for tumor organoids. Organoids were subsequently digested down to single cell suspensions in trypsin-versene according to established protocols (Smalley, 2010). Cells were resuspended in HBS8% BSA. The resulting cell suspensions were filtered through 100 mm cell strainers and analyzed on a BD FACSAria or a Beckman-Coulter MoFlo Cytometer. Dead cells were excluded by propidium iodide fluorescence.

Basal and Myoepithelial Gene Expression.

mRNA expression from relevant probes were identified from a previously published microarray data set by our laboratory (Nguyen-Ngoc et al., 2012). Normal mammary epithelial organoids and mammary tumor epithelial organoids were cultured in 3D collagen for 4 days and harvested for mRNA. Each sample represented at least 3 independent biologic replicates. Sample preparation, labeling, and array hybridizations were performed according to standard protocols from the UCSF Shared Microarray Core Facilities and Agilent Technologies (http://www.arrays.ucsf.edu and http://www.agilent.com). Equal amounts of Cy3-labeled target were hybridized to Agilent whole mouse genome 4×44K Ink-jet arrays (Agilent). Arrays were scanned using the Agilent microarray scanner (Agilent), and raw signal intensities were extracted with Feature Extraction v9.1 software (Agilent). Microarray data was deposited to the NCBI GEO repository and are accessible through GEO series accession number GSE39173.

Oxytocin Contractility Experiment.

Normal mammary epithelial organoids and MMTV-PyMT tumor organoids were embedded in 3D collagen I matrix and cultured in FGF2 organoid media for 4 days. Normal and tumor organoids were then monitored by DIC time-lapse microscopy collecting images every 5 min. Oxytocin (Sigma, 03251) was dissolved to a final concentration of 5 and 50 nM in FGF2 organoid media. The medium was replaced for normal and tumor samples and contraction was observed by time-lapse imaging, again collecting images every 5 min. The area defined by the tissue organoid boundary pre- and postoxytocin treatment was measured using Zeiss software, and plotted using R and the ggplot2 package.

Second Harmonic Generation Microscopy to Measure Collagen Fiber Density.

Tumor sections from 8 tumors were stained for K14, phalloidin and collagen IV. Confocal sections from optically cleared specimens were imaged on a Zeiss 710 with a Chameleon laser set to 880 nm, set to max pinhole. Random fields were collected at 25× resolution and classified into one of three morphologies: K14+ cells with invasive morphology, K14+ cells with noninvasive morphology, or K14− regions. Mean pixel intensity for SHG and collagen IV channels were then determined in Fiji using a custom macro. We defined the zero point to be the mean pixel intensity averaged over all K14− regions, which did not express collagen IV and had weak SHG signal. Mean pixel intensities were then plotted in R using ggplot and are presented as box-plots. Statistics were determined using an unpaired two-sided t test.

Matrix Switching Experiments.

MMTV-PyMT; K14-GFP; mT/mG tumor organoids were cultured in 3D Matrigel for four days, and then freed from the gel by gentle agitation and resuspension in DMEM. Intact tumor organoids were spun down by differential centrifugation and re-embedded in 3D collagen I. Fluorescent tumor organoids were then imaged used a spinning disc confocal microscope in time-lapse mode with membrane Tomato outlining cell membranes, and GFP marking K14+ cells.

Lentiviral Transduction of Tumor Organoids.

Under standard conditions, epithelial organoids have extremely low lentiviral transduction efficiency. We achieved efficient viral transduction in mammary epithelium by using a magnet-based approach, in which magnetic bead-coupled virus is brought into direct contact with organoid structures (Oz Biosciences). Lentiviral particles encoding shRNAs against luciferase, K14, and p63 were purchased at a titer of $1 \times 10^{\wedge}6$ PFU/ml from the MISSION pLKO library (Sigma). Organoids were infected with lentivirus in complex with magnetic nanoparticles, and after a 1-day growth period, were selected with puromycin to enrich for shRNA expressing cells. Selected organoids were then harvested for western blotting or embedded in 3D collagen for time-lapse DIC microscopy.

Mammary Fat Pad Transplantation.

Tumor organoids were harvested and either directly transplanted the following morning or infected and selected following lentiviral transduction. Mammary organoid transplantation was conducted using a JHU IACUC approved protocol. 3-4 week old congenic FVB host mice were anesthetized with isofluorane. Following a midline excision, each #4 mammary gland was exposed, cleared of the fat pad extending to the mammary lymph node, and ~300-500 organoids either in 20 ml of DMEM or 50:50 DMEM/Matrigel were transplanted into the residual fat pad. Cleared areas were treated with bupivicane for analgesia, and the mouse was closed up with surgical staples. Mice were followed for recovery every day for 1 week, and monitored twice weekly thereafter for tumor growth. Mice were generally harvested with tumors exceeding 1 cm in size.

Results

An Ex Vivo 3D Culture Assay Identifies Invasive Cells within Primary Tumors.

We developed a 3D primary culture model (Nguyen-Ngoc et al., 2012) that enabled us to observe cell behaviors during collective invasion and to interrogate the molecular phenotype of the most invasive cells (FIG. 1A). Briefly, we isolate fresh primary tumors and use a combination of mechanical disruption and enzymatic digestion to generate "tumor organoids." Tumor organoids are composed of 200-1,000 adherent tumor cells and reflect the cellular heterogeneity present in the primary tumor. To study collective invasion, we cultured tumor organoids in 3D collagen I gels, a model for the microenvironment surrounding invasive breast cancers (Conklin et al., 2011; Nguyen-Ngoc et al., 2012; Paszek et al., 2005; Provenzano et al., 2008; Wolf et al., 2009).

We first characterized invasion in organoids derived from a genetically engineered mouse model of breast cancer in which the mouse mammary tumor virus long terminal repeat drives expression of the polyoma virus middle T oncogene (MMTVPyMT) (Guy et al., 1992a). MMTV-PyMT mice develop highly invasive mammary tumors that metastasize spontaneously to the lung (Lin et al., 2003). By gene expression profiles, MMTVPyMT tumors cluster with the aggressive lumenal B subtype of human breast cancer (Herschkowitz et al., 2007). Tumor organoids isolated from this model progressively extended multicellular strands of cancer cells into the collagen I over 48-72 hr (FIG. 1B and Movie 8 (not shown)). Because the cells leading these invasive strands were highly protrusive and migratory, we refer to them as "invasive leader cells" (FIG. 1B, right).

Invasive Leader Cells Are Molecularly Distinct and Express Basal Epithelial Markers.

We were able to determine the molecular phenotype of invasive leader cells unambiguously due to their position at the front of invasive strands and their distinct protrusive morphology. Our analysis defined four molecular features of leader cells in this lumenal mouse model. First, leader cells preferentially expressed multiple basal epithelial markers, including cytokeratin-14 (K14), p63, P-cadherin, and cytokeratin-5 (K5) (FIGS. 1C-1G). Among these markers, K14 was the most frequently associated with leader cells (94% of leaders, n=1,523 leaders, from 10 mice, CI [93%-95%]). Second, leader cells coexpressed markers of lumenal epithelium, including K8, K18, and E-cadherin (FIGS. 1G and 8A-8C). However, whereas basal markers were preferentially expressed in leader cells, K8 and E-cadherin also strongly stained the noninvasive K14− core of cells within the tumor organoid (FIGS. 8A and 8C). Third, leader cells typically did not express markers of smooth muscle contractility, such as SMA, MYH11, and CNN1 (FIGS. 1G, and 8D, and 8E) and did not contract in response to the hormone oxytocin, which induces smooth muscle contractility (FIGS. 8F and 8G). Because the smooth muscle program is a defining feature of myoepithelial cells in the normal mammary gland, we conclude that invasive leader cells are distinct from myoepithelial cells. Fourth, leader cells did not typically express Twist, Slug, or vimentin (FIG. 8H), which are common markers of a molecular epithelial-mesenchymal transition (EMT). Finally, leader cells retained membrane localized E-cadherin at sites of cell-cell contact with follower cells (FIG. 8C, blue arrows). Taken together, our observations reveal that invasive leader cells in this lumenal breast cancer model are molecularly distinct from bulk tumor cells and preferentially express K14 and other basal epithelial markers.

K14+ Cells are Enriched at the Invasive Border in Primary Tumor and in Lung Metastases.

We next asked whether K14+ cells also led collective invasion in vivo in this lumenal model. To address this question, we optically reconstructed large regions of the tumor-stromal border from fixed sections of intact tumors. K14+ cells were concentrated at tumor-stromal borders (n=9 reconstructed tumors from 8 mice; FIG. 2A) and led multicellular invasive strands into the adjacent muscle (FIGS. 2A and 2B and Movie 9 (not shown)). As in 3D culture, K14+ cells were negative for SMA and coexpressed lumenal K8 (FIGS. 2B and 9A). Thus, K14+ cells lead collective invasion in 3D culture and in vivo.

We next asked what fraction of collective invasion in vivo was led by K14+ cells. We employed an orthotopic transplant model to mark donor-derived tumor cells unambiguously. We transplanted MMTV-PyMT mammary tumor organoids coexpressing a red fluorescent reporter (mTomato) into the cleared mammary fat pads of nonfluorescent congenic hosts (FVB) and identified invasive units at the tumor-stromal border, blind to K14 expression (FIGS. 2C and 2D). These invasive units included multicellular groups of cells connected to the main tumor mass, which we defined as invasive strands, and groups of cells unconnected from the main tumor mass, which we defined as tumor nests (FIG. 2D, middle). We then classified each invasive unit—in the case of strands, we asked whether the leader cells were K14+, and in the case of nests, we asked whether any cell in the group was K14+. By this measure, we observed that 88% of invasive strands and 80% of tumor nests were K14+(FIG. 2D, right). Next, we systematically quantified the distance of K14+ and K14-cells from the tumor-stromal border in large optically reconstructed montages (FIGS. 9E-9G). We observed strong enrichment for K14+ cells in the first 100 mm from the stromal border, whereas K14− cells were relatively uniformly distributed (n=5 montages from 4 tumors; FIG. 9H). We conclude that K14+ cancer cells are strongly enriched at the tumor-stromal interface and lead the majority of collective invasion in vivo.

Because MMTV-PyMT tumors develop metastases with high penetrance, we next quantified the K14 status of their lung metastases. Although K14 was absent in normal lung parenchyma, we observed K14 staining in >88% of metastatic lesions, from micrometastases up to large, 500 mm lesions (FIGS. 2E-2H). In contrast, K14+ cells constituted only a small percentage of the total cell population in the primary tumor (1.4%±0.2% by fluorescence-activated cell sorting [FACS], n=3 mice; FIG. 9D). Consistent with their phenotype in the primary tumor, K14+ metastases were negative for SMA in both micrometastatic and large metastatic lesions (FIGS. 9B and 9C). We conclude that, although K14+ cells are rare in the primary tumors of this lumenal breast cancer model, they are strongly enriched in lung metastases.

K14+ Cells Lead Collective Invasion across Multiple Mouse Models of Breast Cancer.

To test the generality of our observations, we next characterized invasion in two additional genetically engineered mouse models of breast cancer: MMTV-Neu, a model of HER2+ lumenal breast cancer, and C3(1)/Tag, a model of basal breast cancer (Guy et al., 1992b; Maroulakou et al., 1994). Tumor organoids isolated from these models displayed pronounced differences in the morphologic patterns and timing of invasion in 3D culture (FIGS. 3A and 3B and Movie 10 (not shown)). MMTV-Neu tumor organoids had the fewest leader cells, MMTV-PyMT organoids had an intermediate number, and C3(1)/Tag tumor organoids had the most leader cells (FIGS. 3C and 3D). Despite these differences in the frequency of invasion, >80% of leader cells in all three models were K14+(FIG. 3E). Similarly, the majority of K14+ leader cells coexpressed lumenal K8 but did not express SMA in all three models (FIGS. 3B, 3E, 10A, and 10B).

K14+ Cells Lead Collective Invasion in Primary Human Breast Tumors in 3D Culture and In Vivo.

To validate our observations from mouse models, we next characterized invasive leader cells in fresh human breast tumor specimens. We isolated organoids from primary tumor tissue obtained at initial breast surgery (n=10; FIG. 3F) using established protocols (Nguyen-Ngoc et al., 2012). We classified each specimen using surrogate immunohistochemistry definitions (Goldhirsch et al., 2013). In total, there were nine lumenal breast cancers, five of which were lumenal B. In each case, human tumor organoids invaded into collagen I matrix (FIG. 3F and Movie 10 (not shown)). Although the numbers of invasive strands and disseminated cells varied among tumor samples, >86% of leaders expressed K14 across all samples (FIGS. 3F, 3G, and 10E). K14+ cells typically coexpressed nuclear p63 (FIG. 10C) and typically did not express SMA (FIGS. 3F and 10E). A subset of K14+ cells was also positive for lumenal K8 and K18 (FIG. 10D). Together, these data demonstrate that the cells that lead invasion in 3D culture express basal epithelial markers across multiple mouse models of breast cancer and in primary human breast tumors.

We therefore hypothesized that K14+ cells would lead collective invasion in primary human breast tumors in vivo. We first examined fixed sections from intact tumor specimens corresponding to three cases from 3D culture. We observed that K14+ cells led collective invasion in each case (FIG. 10F). We next assayed for K14+ cells in archival specimens of primary breast tumors (n=39 specimens) from multiple subtypes of human breast cancer. Using consensus guidelines, we then assigned these specimens to breast cancer subtypes based on their ER, PR, HER2/Neu, and Ki-67 status, as assayed by immunohistochemistry (Goldhirsch et al., 2013). There were 16 lumenal A cases, 17 lumenal B cases (including 4 cases with HER2+ disease), and 6 triple-negative breast carcinomas (FIG. 3I). We stained these samples for K14 using immunohistochemistry and classified their intensity to three levels: low (+), medium (++), and high (+++) (FIG. 11A).

We observed strong K14 staining (CK3) in collective invasive fronts in lumenal A, lumenal B (both HER2- and HER2+), and triple-negative breast cancers (FIGS. 3H, 3J, and 11D-11G). Breast cancer subtype was not statistically significantly associated with K14 staining intensity (Fisher's exact test, p=0.11). We also stratified samples by histologic grade (FIG. 3K). In general, higher histologic grade was associated with higher K14 staining intensity (FIG. 3L, Fisher's exact test, p<1×10-4). However, even among lumenal B tumors with high grade (grade 3), we identified cases with low, medium, and high K14 staining (FIG. 11A). We observed three distinct patterns of K14 staining in human tumors: cytoplasmic staining, cytoskeletal staining with intense staining bundles of K14, and a border-enriched pattern, in which staining appeared specific to cells at the border of the collective invasion front (FIG. 11B). The triple-negative breast cancers showed a statistically significant increase in cytoskeletal staining pattern relative to lumenal tumors (FIG. 11C; Fisher's exact test, p<0.01). Together, these data demonstrate that K14 is expressed in collective invasion fronts across the major subtypes of human breast cancer.

Lumenal Tumor Cells Acquire Markers of Basal Differentiation.

To address how K14+ leaders are generated, we asked when K14 was expressed in 3D culture of MMTV-PyMT tumor organoids. Consistent with the low in vivo frequency of K14+ cells in this lumenal mouse model, tumor organoids were initially K8+, with few K14+ cells. During the first 48 hr of culture, the number of K14+ cells and p63+ cells in tumor organoids increased significantly (FIGS. 4A-4D, 12A, and 12B). This expansion in basal marker positive cells coincided closely in time with the onset of collective invasion (FIGS. 4E and 12C). K14+ and p63+ cells were most frequently observed on the basal surfaces of tumor organoids in contact with the extracellular matrix (ECM). Thus, tumor organoids start 3D culture primarily lumenal in character and subsequently expand a population of cells with basal differentiation markers.

One possible cellular mechanism for the expansion of K14+ cells is cell proliferation. However, the number of mitotically active (pH3+) K14− cells was significantly greater than the number of mitotically active K14+ cells during the first 2 days of culture (FIGS. 12D and 12E). Furthermore, treatment with aphidicolin blocked mitosis completely but did not prevent an increase in K14+ cells (FIGS. 4F-4H). We conclude that proliferation is not required for acquisition of a K14+ cell phenotype.

Alternatively, lumenal tumor cells may convert directly from K14− to K14+ states. To test this hypothesis directly, we generated MMTV-PyMT mice carrying a K14 promoter biosensor in which GFP reports on K14 gene expression (Vaezi et al., 2002). In these tumor organoids, we observed individual cells at the basal surface transition from K14− to K14+ states (FIG. 4I, cross-sectional view, and 12F, en-face, and Movie 11 (not shown); n=22 movies). Following phenotypic conversion, the newly K14+ cells dynamically extended and retracted membrane protrusions into the matrix (n=149 movies) and led migration of trailing GFP− cells (n=70 movies; FIG. 4J and Movie 11 (not shown)). Consistent with these data in mouse, we observed that organoids derived from multiple primary human breast tumors similarly expanded their fraction of K14+ and p63+ cells (FIGS. 12G-12I). Taken together, these data reveal that the invasive leader phenotype is a differentiation state exhibited by cancer cells, not a fixed lineage.

K14+ Cells Acquire Leader Cell Behaviors Specifically in Collagen-I-Rich Local Microenvironments.

We previously demonstrated that ECM composition strongly regulates tumor invasion (Nguyen-Ngoc et al., 2012). Organoids isolated from the same tumor but allocated to different ECMs robustly invaded when cultured in collagen I, but not when cultured in basement membrane gels (Matrigel). We therefore hypothesized that different ECM environments might have a differential capacity to induce the basal gene expression characteristic of invasive leader cells.

To test this hypothesis, we cultured MMTV-PyMT tumor organoids in 3D Matrigel. Although tumor organoids were noninvasive in Matrigel (FIGS. 13A-13C), we still observed a robust increase in the number of K14+ tumor cells. At day 0, there were few K14+ cells, but by day 4, 99% of tumor organoids had basal K14+ staining (FIGS. 5A and 5B). As in collagen I, Matrigel-embedded tumor organoids expressed nuclear p63 and P-cadherin specifically in basally located cells in contact with ECM and did not express SMA (FIGS. 5C, 5D, and 13D). Consistent with these results, we also observed phenotypic conversion in K14-GFP; PyMT tumor organoids cultured in Matrigel (FIG. 13E and Movie 12 (not shown); n=5 movies). Taken together, these data demonstrate that induction of the basal epithelial program does not require collagen I and occurs in diverse ECM microenvironments.

If phenotypic conversion induces a stable change in invasive potential, then switching to an invasive microenvironment should induce an acute change in K14+ cell behavior. To test this hypothesis, we conducted a matrix-swapping experiment. We cultured PyMT tumor organoids in 3D Matrigel for 4 days, liberated organoids from the gel, and re-embedded them in collagen I. Under these conditions, there was rapid collective invasion from the basal layer within 12 hr (FIGS. 13F and 13G and Movie 13 (not shown); n=14 movies). In response to collagen I matrix, individual K14+ cells at the basal surface became protrusive and subsequently initiated collective invasion (FIG. 13G, insets). These findings show that phenotypic conversion and collective invasion are distinct steps and that the latent invasive potential of K14+ cells is only converted to invasive cell behaviors in specific tumor microenvironments.

In vivo, we observed that, although K14+ cells led collective invasion, there were also K14+ cells with noninvasive morphology (FIG. 2A). These findings raised the question of which factors in vivo distinguish K14+ cells that manifest invasive morphology from those that do not. Because the local ECM context within a primary tumor is heterogeneous, we hypothesized that differences in invasive morphology in vivo would correlate with differences in ECM context. Accordingly, we assayed fibrillar collagen density in fixed thick tumor sections by second harmonic generation (SHG) and collagen IV density by immunofluorescence. Areas were classified as having either invasive or noninvasive morphology based on the protrusive morphology of the K14+ cells in the region (FIGS. 5E and 5F). Invasive regions were associated with an ~8-fold increase in median collagen I fiber density relative to noninvasive regions (FIG. 5G). In contrast, collagen IV, a component of basement membrane and Matrigel, was observed at comparable levels in both invasive and noninvasive regions (FIG. 5H). Taken together, our data demonstrate that 3D Matrigel and 3D collagen I ECM microenvironments induce distinct cell morphologies similar to those observed in specific regions of primary tumors in vivo and suggest that K14+ cells in vivo acquire leader cell behaviors specifically in collagen-I-rich local microenvironments.

Basal Epithelial Genes K14 and p63 are Required for Collective Invasion in 3D Culture.

We next asked whether expression of basal epithelial genes by leader cells is functionally required for collective invasion. Accordingly, we developed protocols for efficient lentiviral transduction of primary tumor organoids. We tested five different small hairpin RNAs (shRNAs) targeting K14 and p63 and determined the two hairpins with the highest knockdown efficiency by western blotting (FIGS. 14A and 14B). As a control, we used a hairpin-targeting luciferase (Luc-kd).

To assess the requirement for K14 in collective invasion, we cultured Luc-kd, K14-kd1, and K14-kd2 tumor organoids in 3D collagen I and observed them by time-lapse differential interference contrast (DIC) microscopy. Control Luc-kd organoids strongly expressed K14 and invaded vigorously into collagen I matrix (FIGS. 6A-6C and Movie 14 (not shown)). In contrast, both K14 expression and collective invasion were markedly reduced in K14-kd organoids (FIGS. 6A, 6B, 6D, and 6F). Although K14– kd tumor organoids generally lacked multicellular invasive strands, we still observed subcellular protrusions extending from K14-kd organoids (FIG. 6D, red arrows, and FIG. 14C). We next infected organoids with lentiviruses encoding both K14-shRNA and GFP to label K14-kd cells in real time. By tracking infected organoids at single-cell resolution, we observed individual K14-kd cells that were protrusive and motile (FIG. 6H). Thus, we conclude that K14 is dispensable for subcellular protrusions but is required for the transition to persistent collective invasion.

We next examined the phenotypic consequences of p63 knockdown (p63-kd1 and p63-kd2) in PyMT primary tumor organoids cultured in collagen I (FIGS. 6A, 6B, 6E, and 6G). We observed a strong reduction in p63 protein levels and in collective invasion in p63-kd organoids (FIGS. 6E, 6G, and 14D). However, compared with K14-kd organoids, p63-kd organoids had fewer protrusive cells and more rounded cell borders (FIGS. 6E and 14C and Movie 14 (not shown)). Because knockdown with p63 hairpin abrogated collective invasion but yielded only a partial reduction in K14, these data suggest that p63 has essential K14-independent functions in collective invasion. In aggregate, these data demonstrate that multiple basal epithelial genes expressed by leader cells are individually required for collective invasion in 3D culture. Furthermore, these data show that basal epithelial genes are required for collective invasion in a lumenal mouse model of breast cancer, despite being expressed in only a small minority of the tumor cells.

In Vivo Knockdown of K14 Disrupts Collective Invasion at the Tumor-Stromal Border.

We next sought to test the requirement for K14 in collective invasion in vivo. We isolated tumor organoids from fluorescently labeled advanced carcinomas (mTomato+; MMTV-PyMT), transduced them with Luc-kd, K14-kd1, or K14-kd2 lentivirus, and then orthotopically transplanted the transduced organoids into the cleared mammary fat pads of nonfluorescent congenic hosts (FIG. 7A). Although tumor growth appeared similar, we observed strong differences in collective invasion at the tumorstromal border. In Luc-kd tumors, cells at the tumor stromal border strongly expressed K14 and organized many K14+-infiltrating invasive strands and nests of cells (FIG. 7B). In contrast, in K14-kd1 tumors, we observed large regions in which the tumor stromal border was K14– and lacked either invasive strands or nests (FIGS. 7C and 7D). The K14– regions instead displayed borders with a rounded morphology (FIGS. 7C and 7D). Furthermore, whereas fibrillar collagen was associated with collective invasion in control tumors (FIG. 5E), in K14-kd1 tumors, this association was disrupted. Within K14-kd1 tumors, we observed noninvasive borders that were both K14– and surrounded by dense fibrillar collagen (FIG. 7F). To quantify the differences in collective invasion between knockdown conditions, we determined the number of invasive strands and nests per tumor section. The number of collective invasive units per section was significantly reduced in K14-kd1 tumors relative to Luc-kd control tumors (FIG. 7D). Consistent with the less efficient knockdown of K14-kd2 observed by immunofluorescence and western blotting, we observed a qualitatively similar reduction in invasive units in K14-kd2 tumors (FIGS. 7D and 7E). The residual invasion observed in both K14-kd1 and K14-kd2 tumors was predominantly K14+ and was concentrated in discrete K14+ tumor foci (FIGS. 7E and 7G). These data demonstrate the presence of residual tumor cells competent to express K14 and suggest that, despite puromycin selection prior to transplantation, K14-competent cells preferentially expanded in vivo. Together, these data demonstrate (1) that K14 is required in vivo for collective invasion at the tumor-stromal border, (2) that elevated collagen I is not sufficient to induce collective invasion in vivo in the absence of K14 expression, and (3) that targeting a basal invasive program expressed in a small minority of tumor cells is sufficient to disrupt the invasive process in an advanced carcinoma.

DISCUSSION

The transition to invasive behavior in epithelial cancer cells is a critical step in metastasis, yet both the cellular and molecular basis of this transition is incompletely understood. An important challenge is that primary tumors are complex heterogeneous tissues containing phenotypically and genetically distinct cancer cell subpopulations interacting with an altered extracellular matrix and diverse stromal cells (Almendro et al., 2013; Egeblad et al., 2010a, 2010b; Fidler, 2003; Weigelt and Bissell, 2008). It is important to reduce this complexity to specific molecular regulators of tumor cell behavior in order to identify targets for therapeutic intervention.

To accomplish this goal, we developed a general strategy for identifying the most invasive cells in a primary epithelial tumor. We then applied this strategy and discovered that the most invasive cancer cells are behaviorally and molecularly distinct from bulk tumor cells. Importantly, the invasive leader cells expressed basal epithelial genes, including K14 and p63, across mouse models of breast cancer and in diverse human breast tumors. Cells with this phenotype led the majority of collective invasion in vivo and were strongly overrepresented in lung metastases. We therefore have exploited our assays to resolve the heterogeneous cancer cell populations within the primary tumor into functional classes based on their invasive behavior. We then leveraged this understanding to establish the requirement for K14 and p63 for collective invasion in primary cells derived from poorly differentiated carcinomas.

Previous studies have shown that heterotypic epithelial-stromal interactions contribute to cancer invasion in diverse malignancies (Condeelis and Pollard, 2006; Gaggioli et al., 2007). Our data establish the importance of heterotypic epithelial epithelial interactions between different cancer cell subpopulations in collective invasion Importantly, although invasive leader cells were highly protrusive and migratory, they retained characteristically epithelial expression of cell adhesion proteins (e.g., E-cadherin) and intermediate filament proteins (e.g., K14, K8) during invasion.

K14 expression also marks other highly migratory epithelial cell populations. During development, the migratory cells of the normal mammary embryonic placode are K14+K8+SMA– (Moumen et al., 2011; Sun et al., 2010). Similarly, the highly invasive rat breast cancer MTLn3 cell line is K14+K8+, whereas noninvasive MTCs do not express these markers (Lichtner et al., 1991). Likewise, highly invasive human breast cancer cell lines MDA-MB-468, MDA-MB-436, and BPLER are K14+K18+, whereas cell lines with low invasive potential, such as MCF-7, T47D, and ZR75 express a pure lumenal phenotype (Gordon et al., 2003; Petrocca et al., 2013). Experimental models suggest that basal breast cancers arise from lumenal progenitors and that mutations in genetic drivers of breast cancer, such as BRCA1, can shift lumenal progenitors toward basal differentiation (Lim et al., 2009; Molyneux et al., 2010). Consistent with these observations, a number of pathologic studies have shown that basal cytokeratins, including K14, are associated with poor patient prognosis, early relapse, and reduced overall survival (de Silva Rudland et al., 2011; Gusterson et al., 2005; Laakso et al., 2006; Malzahn et al., 1998). Our study provides a biological basis for these findings, namely that K14 marks a subpopulation of tumor cells capable of initiating collective invasion, a critical step in metastatic progression.

Importantly, we directly observed phenotypic conversion of K14− lumenal tumor cells to K14+ cells with invasive potential. We previously demonstrated that collective invasion is strongly regulated by the composition of the local extracellular matrix (Nguyen-Ngoc et al., 2012). In the present study, we demonstrated that the basal invasive program can be induced in diverse ECM microenvironments. However, consistent with our prior study, basal gene expression was only associated with invasive cell behaviors and morphologies in collagen-I-rich microenvironments in 3D culture and in vivo.

In our study, we established that the basal epithelial intermediate filament cytoskeleton is specifically required for collective invasion in cancer. Our data suggest that actin-based subcellular protrusions and multicellular collective invasion can be uncoupled and have distinct cytoskeletal requirements. The precise mechanism by which cytokeratin 14 regulates collective invasion, be it directly modifying the tensile strength and viscoelastic properties of the cell (Yamada et al., 2002), regulating cell-cell adhesion (Weber et al., 2012), or by signal transduction mechanisms independent of their mechanical properties (Kim et al., 2006), remains unclear and warrants further study. Because cells with basal differentiation are found in many epithelial organs, our findings may also have implications for invasion in other solid tumors.

Generation of an HCC Organoid 3D Model.

Based on our past experience with breast tumors, we developed methods to isolate and culture organoids derived from primary hepatocellular carcinomas (HCC). Briefly, we surgically remove the tumor, chop coarsely with a sterile razor blade, incubate with collagenase and trypsin, then separate the epithelial organoids from the stromal single cells by differential centrifugation (FIG. 20). We recover 500-2500 organoids per tumor and explant into 3D Matrigel or collagen I. Media conditions were based on embryonic hepatocyte cultures. We have developed robust isolation and 3D culture conditions and have optimized our antibodies for formalin fixed paraffin embedded (FFPE) sections.

We observed microenvironment specific invasion. In Matrigel, HCC tumors were indolent. In collagen I gels, HCC organoids invaded vigorously. Collagen I represents the more appropriate model for the fibrotic conditions associated with HCC in patients. We can also incorporate tumor derived fibroblasts and immune cells and assay for effects on proliferation and invasion.

Only a small minority of the cancer cells in a HCC in vivo are located at the invasive edge (FIG. 21). Our HCC organoids are derived from throughout the tumor and so the average cancer cell in an organoid was not likely to be actively invading in vivo at the time of tissue isolation. Yet, virtually all HCC organoids invade into collagen I within a week. We therefore anticipate a broad upregulation of invasive genes, as we have seen with primary breast cancer organoids.

We claim:

1. A method comprising the steps of:
   a. isolating a primary tumors from a subject;
   b. generating tumor organoids via mechanical disruption and enzymatic digestion;
   c. separating tumor organoids from single cells using differential centrifugation;
   d. embedding the tumor organoids in an extracellular matrix gel; and
   e. measuring gene expression and/or protein levels in the cells leading the invasive strands of the tumor organoids.

2. The method of claim 1, wherein the extracellular matrix gel is a collagen I gel.

3. The method of claim 1, wherein the extracellular matrix gel is a three-dimensional extracellular matrix gel.

4. A method comprising the steps of:
   a. isolating tissue from a patient's tumor;
   b. generating tumor organoids via mechanical disruption and enzymatic digestion of the tissue;
   c. separating tumor organoids from single cells using differential centrifugation;
   d. embedding the tumor organoids in an extracellular matrix gel; and
   e. performing an invasion assay on the tumor organoids.

5. The method of claim 4, wherein the extracellular matrix gel is a collagen I gel.

6. The method of claim 4, wherein the extracellular matrix gel is a three-dimensional extracellular matrix gel.

7. The method of claim 4, further comprising the step of measuring gene expression and/or protein levels in the cells leading the invasive strands of the tumor organoids.

\* \* \* \* \*